(12) United States Patent
Schick et al.

(10) Patent No.: US 6,910,503 B2
(45) Date of Patent: Jun. 28, 2005

(54) METHODS AND APPARATUS FOR MICRO-FLUIDIC ANALYTICAL CHEMISTRY

(75) Inventors: Hans G. Schick, Concrete, WA (US); Michael L. Bailey, Oak Harbor, WA (US); Thomas C. Dykas, Bellingham, WA (US)

(73) Assignee: Upchurch Scientific, Inc., Oak Harbor, WA (US)

( * ) Notice: Subject to any disclaimer, the term of this patent is extended or adjusted under 35 U.S.C. 154(b) by 13 days.

(21) Appl. No.: 10/628,829

(22) Filed: Jul. 28, 2003

(65) Prior Publication Data

US 2004/0134546 A1 Jul. 15, 2004

Related U.S. Application Data

(63) Continuation-in-part of application No. 10/154,879, filed on May 24, 2002, now Pat. No. 6,729,350.
(60) Provisional application No. 60/293,654, filed on May 25, 2001.

(51) Int. Cl.$^7$ .............................................. E03B 00/00
(52) U.S. Cl. ................................ 137/625.47; 73/864.83
(58) Field of Search .................... 137/625.47; 73/23.42, 73/61.56, 61.59, 864.83

(56) References Cited

U.S. PATENT DOCUMENTS

| | | | | |
|---|---|---|---|---|
| 4,444,066 A | * | 4/1984 | Ogle et al. ............... | 73/863.72 |
| 4,756,201 A | * | 7/1988 | Uffenheimer ............ | 73/864.83 |
| 5,270,212 A | * | 12/1993 | Horiuchi et al. .............. | 436/45 |
| 5,544,276 A | * | 8/1996 | Loux et al. .................. | 392/480 |
| 5,575,929 A | * | 11/1996 | Yu et al. ....................... | 216/10 |
| 5,583,281 A | * | 12/1996 | Yu ............................ | 73/23.42 |
| 5,804,701 A | * | 9/1998 | Berger ....................... | 73/23.42 |
| 6,029,499 A | * | 2/2000 | Sittler et al. ............... | 73/23.42 |
| 6,415,670 B1 | * | 7/2002 | Ohkura et al. ........... | 73/864.83 |
| 6,612,153 B2 | * | 9/2003 | White et al. ............... | 73/23.42 |
| 6,701,774 B2 | * | 3/2004 | Srinivasan et al. ........ | 73/23.42 |
| 6,732,567 B2 | * | 5/2004 | Briscoe et al. ............ | 73/23.39 |
| 6,762,057 B1 | * | 7/2004 | Gilton ........................ | 436/161 |

* cited by examiner

*Primary Examiner*—John Fox
(74) *Attorney, Agent, or Firm*—Vinson & Elkins L.L.P.

(57) ABSTRACT

Improved valve and methods for analytical techniques and systems. The valve includes a main housing, together with a rotor and stator. The stator has openings therethrough which allow for fluid communication between tubing when connected to the valve, and one surface of the rotor. Ferrules can be used with a clamping assembly to tightly connect the tubing to the valve in a way which separates the clamp assemblies (for ease of connection and disassembly), yet still provides close proximity between the fluid connections. In one embodiment, a series of two or more discrete elements, which can be selectively moved relative to one another, are located within the valve in a "stacked" configuration. Each of the discrete elements includes at least one feature useful for performing chemical analysis, such as sample loops, columns, detectors, mixers and the like, all of which are useful in chromatography.

20 Claims, 23 Drawing Sheets

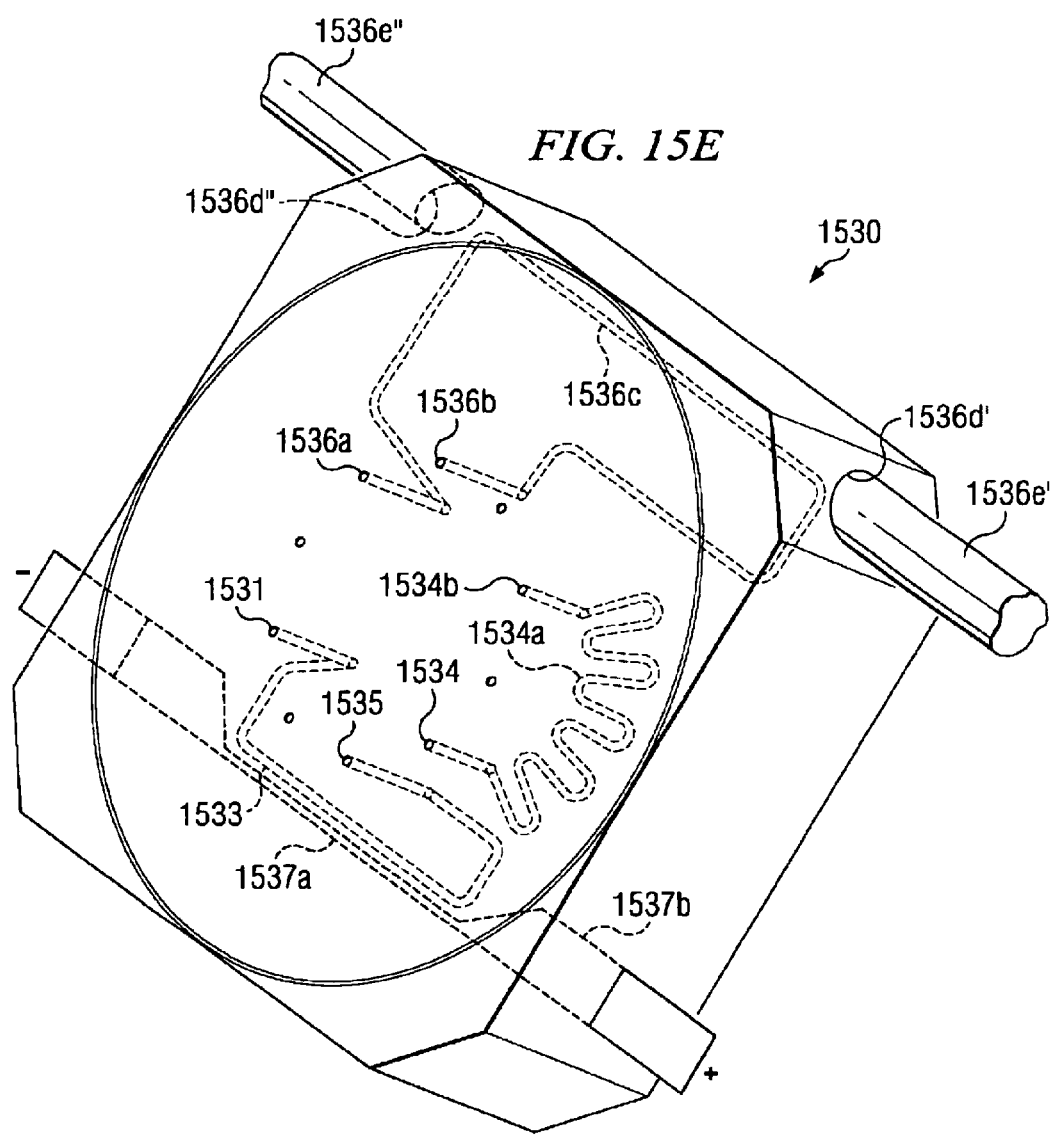

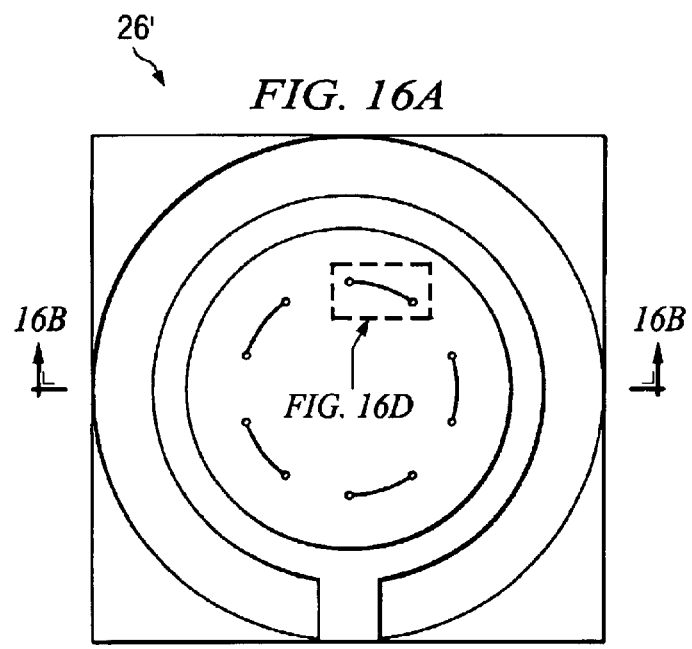
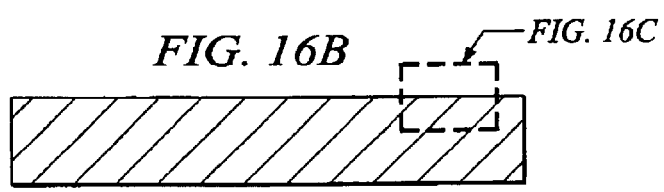
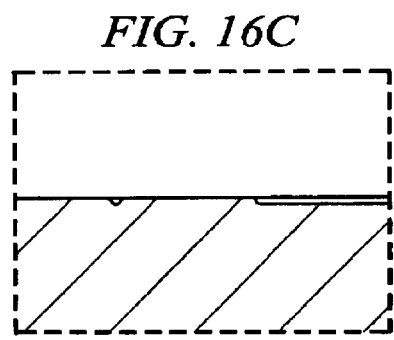

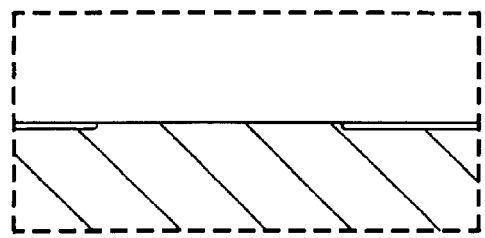
*FIG. 16G*
*FIG. 17*
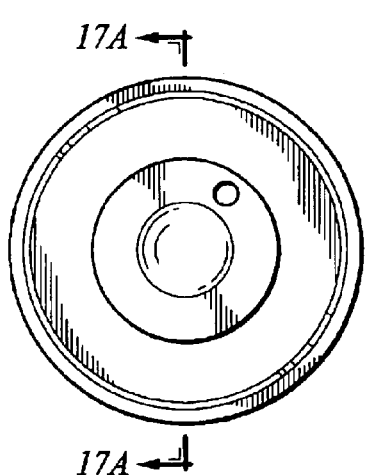
17A ←
17A ←
*FIG. 17A*
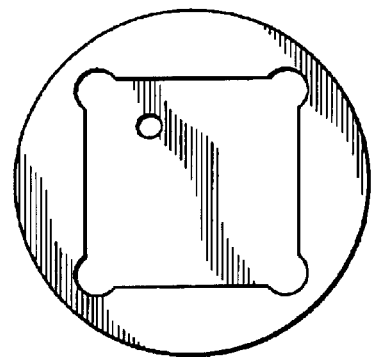
*FIG. 17B*
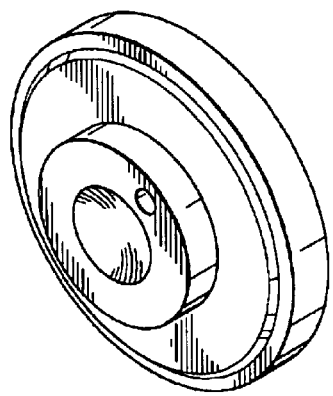
*FIG. 17C*
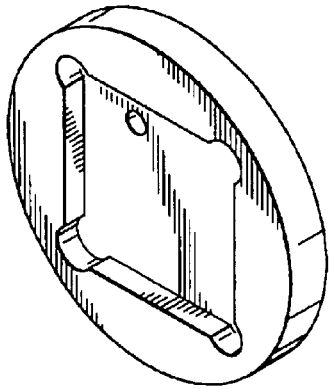
*FIG. 17D*

METHODS AND APPARATUS FOR MICRO-FLUIDIC ANALYTICAL CHEMISTRY

CROSS-REFERENCE TO RELATED APPLICATIONS

This application is a continuation-in-part of U.S. patent application Ser. No. 10/154,879 filed May 24, 2002, now U.S. Pat. No. 6,729,350, which claims priority to U.S. Provisional Patent Application Ser. No. 60/293,654, filed May 25, 2001.

FIELD OF THE INVENTION

This invention relates to an apparatus and methods involving the use of a valve which comprises a ferrule and clamp assembly and/or two or more "stacked" elements for analysis and/or selection of fluid streams and/or injection of fluids in analytical processes such as liquid chromatography and mass spectrometry. In particular, the invention relates to a valve (such as an injection valve or a selection valve) that comprises a ferrule and clamp assembly and/or comprises two or more discrete elements, such as a sample loop element, a separation element, a mixing element, a flow splitting element, and/or an electric potential or light source or other information element, and the like, in a manner which allows for analysis of extremely small samples.

BACKGROUND OF THE INVENTION

Multiport selector/injector valves are well known and have been used in a variety of industrial processes, such as liquid chromatography and mass spectrometry. For example, selection valves are commonly used in liquid chromatography and other analytical methods to direct fluid flow along alternate paths. Such valves are also used to terminate fluid withdrawal from one source and select another source of fluid, for example, such as when a variety of streams in an industrial process is selectively sampled for analysis.

Injector/selector valves are often used in high pressure liquid chromatography (HPLC) or gas chromatography (GC). U.S. Pat. No. 4,242,909 (Gundelfinger '909), which is hereby fully incorporated by reference, describes sample injection apparatus for withdrawing liquid samples from vials and injecting them into a chromatographic column or other analyzing device. The apparatus is said to minimize wastage, cross contamination, and dilution of the samples, and to be capable of automation with a minimum of complexity. Injector/selector valves are particularly useful in chromatographic applications since a substantial amount of time and effort is required to set up a particular HPLC or GC system, which may often utilize multiple columns and/or multiple detection systems. Multiport selection valves permit the operator of the chromatograph to redirect flows such that particular samples are selected for injection into a particular column, or alternatively, to direct the output from a particular column to one or more different detectors.

As mentioned above, multiport selection valves have been known for some time, including those which utilize a cylindrical rotor and stator combination. In some of these valves, the stator holds the fluid tubes in fixed relation to each other and presents the tube ends to a rotor face which may contain a grooved surface. By varying the angle of the rotor, the tubes are selectively brought into fluid communication. One type of injector/selector valve using a rotor/stator combination is the Type 50 rotary valve from Rheodyne, Incorporated. The Type 50 valves are said to operate by rotation of a flat rotor against a flat stator (see "Operating Instructions for Type 50 Teflon Rotary Valves," Rheodyne, Incorporated, printed in U.S.A. April 1994). Another rotor/stator selector valve is shown in U.S. Pat. No. 5,193,581 (Shiroto, et al.), which is hereby fully incorporated by reference. The valve is said to comprise, among other things, a stator plate having a plurality of outlet holes extending through the stator plate and arranged in a circle concentric with a valve casing, and a rotor having a U-shaped passage formed in the rotor. The rotor is said to be rotated through a desired angle so that an inlet hole can be in fluid communication with selected ones of the outlet holes through the U-shaped passage of the rotor.

U.S. Pat. No. 5,419,419 (Macpherson) describes a rotary selector valve that is used in connection with an automatic transmission in an automobile. A motor is said to index a shear plate of the selector valve to predetermined positions for shifting the transmission. A series of working lines as shown in FIG. 6 are maintained in a closed spatial relationship with the casing.

U.S. Pat. No. 3,494,175 (Cusick, et al.) discloses a valve having a plurality of capillaries which are held in spaced relationship within a manifold plate member. U.S. Pat. No. 3,752,167 (Makabe) discloses a fluid switching device including a plurality of capillaries that are held within threaded holes by couplings. A rotary member allows fluid communication between the tubes. U.S. Pat. No. 3,868,970 (Ayers, et al.) discloses a multipositional selector valve said to be adapted with a means for attaching a plurality of chromatographic columns to the valve, such that the flow can be directed into any of the columns. U.S. Pat. No. 4,705,627 (Miwa, et al.) discloses a rotary valve said to consist of two stator discs and a rotor disposed between the two stator discs. Each time the rotor is turned intermittently it is said, different passages are formed through which the fluid in the valve runs. U.S. Pat. No. 4,722,830 (Urie, et al.) discloses multiport valves. The multiport valves are said to be used in extracting fluid samples from sample loops connected with various process streams.

In many applications using selector/injector valves to direct fluid flows, and in particular in liquid and gas chromatography, the volume of fluids is small. This is particularly true when liquid or gas chromatography is being used as an analytical method as opposed to a preparative method. Such methods often use capillary columns and are generally referred to as capillary chromatography. In capillary chromatography, both gas phase and liquid phase, it is often desired to minimize the internal volume of the selector or injector valve. One reason for this is that a valve having a large volume will contain a relatively large volume of liquid, and when a sample is injected into the valve the sample will be diluted, decreasing the resolution and sensitivity of the analytical method.

Micro-fluidic analytical processes also involve small sample sizes. As used herein, sample volumes considered to involve micro-fluidic techniques can range from as low as volumes of only several picoliters or so, up to volumes of several milliliters or so, whereas more traditional LC techniques, for example, historically often involved samples of about one microliter to about 100 milliliters in volume. Thus, the micro-fluidic techniques described herein involve volumes one or more orders of magnitude smaller in size than traditional LC techniques. Micro-fluidic techniques can also be expressed as those involving fluid flow rates of about 0.5 ml/minute or less.

In the design of selector or injector valves with minimal internal volume, the conventional design consideration is to bring all of the fluid passages into the closest possible proximity to each other. To do this with conventional capillary connectors is very difficult, since the nuts of the connectors are relatively large and require a fair amount of space. Thus, the valve itself has to be relatively large in order to accommodate the connections.

One solution to the large connectors has been to drill the injector ports on an angle. By angling the injector ports, the ends of the channels can all emerge in close proximity to a common point, while the opposite ends of the channels are sufficiently spaced apart to accommodate the larger connectors. An example of this approach is shown in U.S. Pat. No. 5,419,208 (Schick), which is hereby fully incorporated by reference. However, this approach has certain drawbacks. First, angled holes are difficult to produce and expensive to machine. Further, the angled passage from the capillary connector to the center of the valve stator is longer than it would be if the capillary could be connected directly on the face of the valve in close proximity to other capillaries. This additional length creates additional dead volume, which is undesirable as noted above. A further disadvantage of this approach is that the emerging hole near the center of the valve stator has an elliptical shape, which is not desirable.

Another type of capillary connection is shown in U.S. Pat. No. 4,792,396 (Gundelfinger '396), which is hereby fully incorporated by reference. Gundelfinger '396 describes a frame used as part of an injector said to be useful in loading a sample at high pressure into a chromatographic column. The frame is said to comprise ferrules for sealing tubes, and it is said that a tube coupling hole in the frame can couple to a standard 1/16" tube, but also can couple to a much smaller diameter tube useful for minimizing dispersion when small samples or small chromatographic columns are used. The use of ferrules to make capillary or tubing connections to chromatography apparatus is also shown in, for example, U.S. Pat. No. 5,674,388 (Anahara), U.S. Pat. No. 5,744,100 (Krstanovic), U.S. Pat. No. 5,472,598 (Schick), U.S. Pat. No. 5,482,628 (Schick), and U.S. Pat. No. 5,366,620 (Schick), each of which is hereby fully incorporated herein by reference. Of course, to the extent of any conflict in the terminology or descriptions between any of the patents incorporated by reference herein and the text herein, the text hereof shall control.

Still another approach involves the use of "ferrule clusters," as described and explained in my copending U.S. Pat. No. 6,267,143 B1, which is hereby fully incorporated by reference. The ferrule clusters minimize dead volume, but require the connection (or disconnection, as the case may be) of two or more capillaries to (or from) the valve at a time.

It would be desirable to have a selector/injector valve that can be made with the smallest possible valve volume. There is also a need for an injector/selector valve which brings capillary or tube ends into the closest possible proximity to each other and to the valve stator so that valve dead volume is minimized. There is also a need for a capillary connector system that can be used to connect capillaries in the closest possible proximity. Moreover, there is a need for apparatus and methods which allow an operator greater flexibility in selectively connecting and/or disconnecting capillaries to a valve while still meeting the other objectives. However, even a valve which meets such criteria will have dead volumes. For micro-fluidic analyses, there is still a need for apparatus and methods which still further reduce dead volumes.

In conventional LC and GC systems, tubing is used to connect the injector/selector valve with a column (conventionally used to separate the constituents of the sample) and a detector (conventionally used to determine what constituents are present in the sample moving past or through the detector as time passes). In conventional LC and GC systems, the column and the detector are connected by tubing, which may be several inches or even longer lengths. Of course, the greater the distances of tubing through which the sample and its constituents must pass while traveling through the LC or GC system, the greater the amount of "dead volume" present in the system. As noted above, such dead volume is undesirable.

SUMMARY OF THE INVENTION

The invention relates to a multi-port injection/selection valve that comprises two or more discrete elements of an analytical system that can be selectively engaged or disengaged by an operator. In a first embodiment of the invention, a selection/injection valve comprises a series of ports which are in fluid communication with at least a portion of a first element within the valve. This first element, in turn, is in fluid communication with one or more additional discrete elements. Each of these elements comprises one or more features useful in analytical processes, including sample loops, columns, mixers, detectors, and temperature control elements. Moreover, in alternative embodiments, two or more of such features can be provided in a single element. Each of the elements can be independently positioned by an operator to selectively engage or disengage that particular element and its feature(s).

In another embodiment, the invention comprises a clamp and ferrule assembly configuration to connect tubes or capillaries to a common port, or to each other, in the valve. The clamp and ferrule assemblies connect the tubes or capillaries to the body of the valve assembly. The use of the individual clamp and ferrule assemblies, as opposed to conventional connectors, permits the capillary ends to be positioned in extremely close proximity to the valve rotor and to each other, thus minimizing the space between two capillaries when they are in brought into fluid communication with each other (often referred to as the "dead volume" in the connection). The clamp and ferrule assemblies of the present invention also allow an operator to connect, or disconnect, one or more capillaries without connecting, or disconnecting the other capillary connections to the valve.

In one embodiment the invention is a valve, comprising: a) a plurality of clamp and ferrule assemblies, each having a ferrule and a clamp for removably attaching a capillary tube to the valve; b) a stator in contact with at least one of said ferrules, said stator having a stator front side and a stator flat surface opposite said front side, said stator front side having a plurality of impressions into which some or all of said ferrules are received, each of said impressions opening to a terminal cylindrical bore (tube pocket), each of said impressions also having a stator through-hole opening onto said stator flat surface; c) a plurality of capillary tubes, each of said capillary tubes extending through at least one of said ferrules and into a stator impression up to the terminus of said cylindrical bore; and d) a rotor comprising a stator-contact surface and at least one fluid communication channel, said stator-contact surface abutting said stator flat surface and being rotatable about an axis to establish fluid communication between selected pairs of capillaries through said fluid communication channel.

In yet other embodiments of the invention, each of the elements has appropriate grooves for fluid flow that are etched into a glass, quartz, or other surface via photolithographic or other similar etching techniques. In still other embodiments of the invention, the invention is a chromatographic system comprising the valve of the invention. In still other embodiments, the invention is a method for carrying out a chromatographic or spectrometric analysis, and methods for connecting and disconnecting various elements in a chromatographic or mass spectrometry system.

BRIEF DESCRIPTION OF THE DRAWINGS

FIG. 15E shows one element of an embodiment of the invention.

FIG. 16A is a top view of an alternative embodiment of a rotor 26' for a valve in accordance with the present invention.

FIG. 16B is a sectional view of the alternative rotor 26' taken along line 16B—16B.

FIG. 16C is a detailed sectional view of a portion of the alternative rotor 26'.

FIG. 16G is a detailed sectional view of a portion of the alternative rotor 26'.

FIG. 17 is a top view of an alternative embodiment of a rotor mount 33' for a valve in accordance with the present invention.

FIG. 17A is a sectional view of the rotor mount 33' taken along line 17A—17A.

FIG. 17B is a bottom view of the rotor mount 33'.

FIG. 17C is a perspective view showing the top of the rotor mount 33'.

FIG. 17D is a perspective view showing the bottom of the rotor mount 33'.

DETAILED DESCRIPTION

Figure 1:
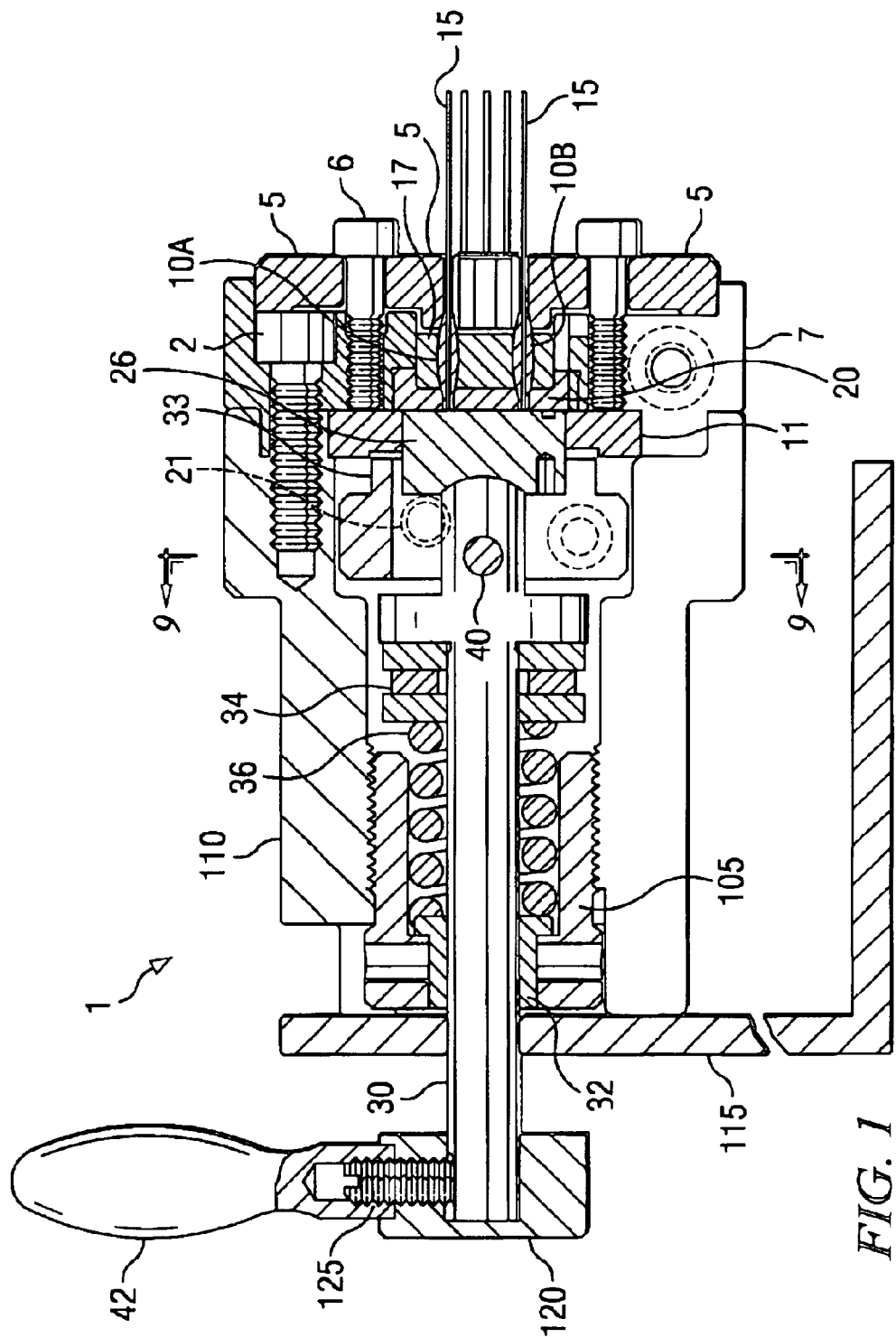
FIG. 1 is a sectional view showing a valve according to one embodiment of the invention.

As seen in FIG. 1, one embodiment of the invention comprises a valve 1 which has plurality of capillaries 15 attached with corresponding ferrules 10A and 10B. The ferrules 10A and 10B of the invention maybe of the double-ended type, as shown in FIG. 1 and in FIG. 7. The double-ended type approximates two single-ended ferrules with their ends joined. Thus, the double-ended ferrules 10A and 10B each have tapered gripping portions on both of their respective ends. As shown in FIG. 1, each of the capillaries 15 extend through an opening in a corresponding clamp 5, through a corresponding ferrule 10, which itself extends through a corresponding opening in ferrule support 17, and through stator 20, such that one end of each of the capillaries 15 are in fluid communication with a front surface of rotor 26. These components of valve 1 and their various features are described below in more detail. It will be understood by those of ordinary skill that the valve 1 allows for the connection of a plurality of capillaries 15 in a manner which minimizes the dead volume between the ends of the capillaries 15, while at the same time allowing an operator to connect or disconnect one or more capillaries 15 to or from valve 10 without having to connect or disconnect all capillaries 15 at the same time.

Referring still to FIG. 1, it can be seen that valve 1 also includes a main body 110, a mounting bracket 115, a handle 42, a set screw 125 (for attaching the handle 42 to the knob 120), and a knob 120. The handle 42, set screw 125, and knob 120 are assembled and attached to one another so that, when an operator, turns handle 42, that action results in corresponding rotation of the shaft 30 and rotor 26. Those skilled in the art will understand and appreciate that handle 42 can be attached or secured to shaft 30 via other means or can be combined into a unitary item with shaft 30. Those skilled in the art will also understand and appreciate that handle 42 is useful for manual operation of the valve 1 by an operator, but the selective rotation of shaft 30 can be automated with conventional means. Those skilled in the art will further understand and appreciate the use of the adjustment nut 105 and the spring 36 to bias shaft 30 against rotor 26 to ensure that the valve 1 operates without any leaking, even at high pressures. Still referring to FIG. 1, it can be seen that each of the cap screws 6 can be tightened by an operator to bias and press the corresponding ferrule 10 and capillary 15 against the facing or abutting surface of rotor 26. This further ensures leak-free operation of the valve.

Figure 2:
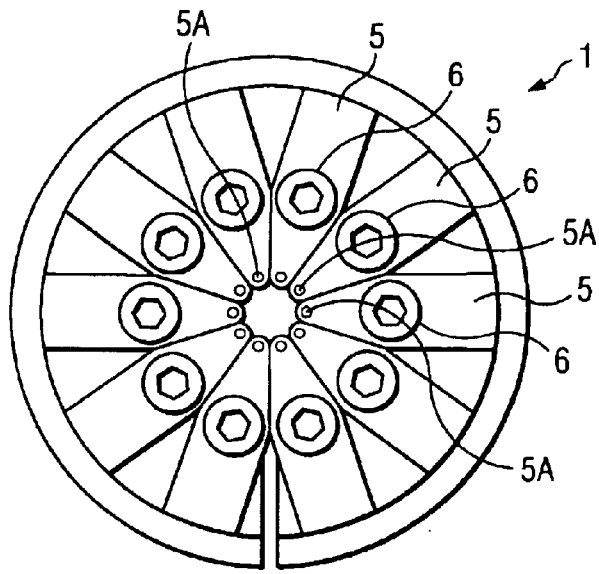
FIG. 2 shows a front view of the valve of one embodiment of the present invention.
Figure 9:
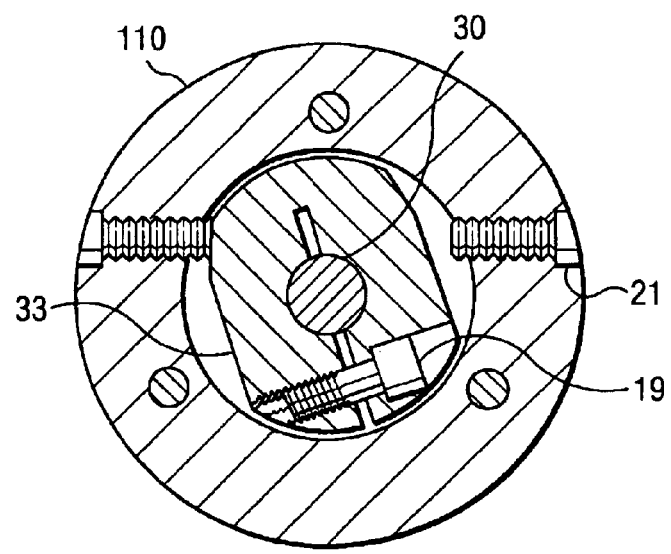
FIG. 9 is a sectional view of a valve taken along line 9—9.

Referring now to FIG. 2, a "frontal" view of valve 1 is shown. As shown in FIG. 2, a plurality of clamps 5 are disposed on the front of valve 1. Those skilled in the art will understand that there may be more or less than ten (10) clamps 5. In FIG. 2, there are ten (10) of clamps 5. Each of clamps 5 has an opening 5a through which a capillary 15 may extend (not shown in FIG. 2). Also as shown in FIG. 2, there is a cap screw 6, a portion of which extends through the corresponding clamp 5. Those of ordinary skill will understand and appreciate that the openings 5a of clamps 5 are located in close proximity to one another, thereby minimizing the dead volume of the fluid communication between capillaries 15 when attached to valve 1 of the present invention. With the ten (10) clamps 5 configuration shown in FIG. 2, for example, we have been able to arrange the ten (10) openings 5a in a circle with a diameter of only 6 mm. As also shown in FIG. 2, the cap screws 6 (like the openings 5a) are arranged in a circle, but the diameter of the circle formed by cap screws 6 is greater than the circle arrangement of the openings 5a. This arrangement makes it easier for an operator to tighten or loosen each of the individual cap screws when connecting or disconnecting a capillary 15. While cap screws 6 are shown, those skilled in the art will understand that other screws, threaded bolts, and fastening means may be used.

Figure 3A:
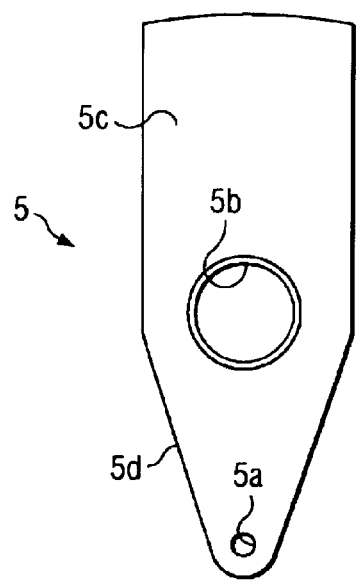
FIG. 3A shows a frontal view of a clamp in accordance with one embodiment of the present invention.
Figure 3B:
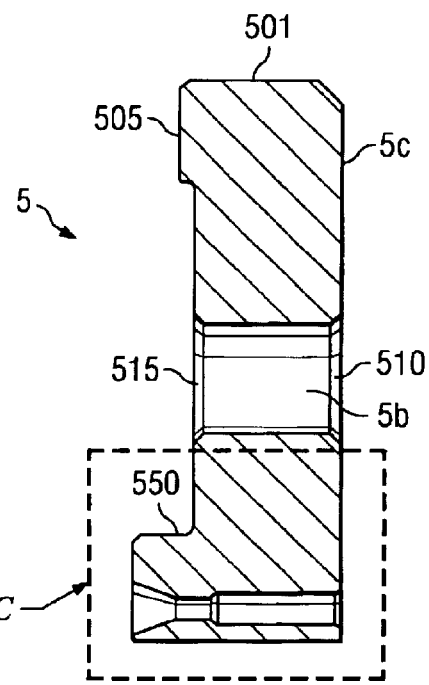
FIG. 3B shows a sectional view of the clamp shown in FIG. 3A.
Figure 3C:
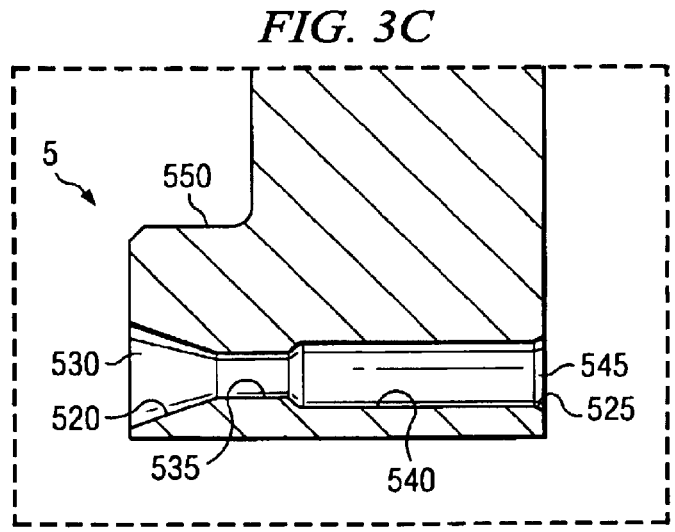
FIG. 3C shows a detailed, fragmentary sectional view of the clamp shown in FIG. 3A.

Referring now to FIGS. 3A, 3B, and 3C, a clamp 5 in accordance with the present invention is shown in greater detail. Referring first to FIG. 3A, a frontal, or overhead, view of a clamp 5 is provided. (For ease of reference, the same numbers are used in various drawings to indicate the same items or features which may be identified in other drawings.) As shown in FIG. 3A, clamp 5 has a main body 5c and also a tapered end 5d. While opening 5a may vary in size depending on the capillary 15 to be received, the valve 1 shown and described as the preferred embodiment has openings 5a which are 2 mm in diameter. The opening 5a for a capillary 15 (not shown in FIG. 3A) is located in the tapered end 5d of a clamp 5. As also shown in FIG. 3A, the clamp 5 has an opening 5b through which a portion of a cap screw 6 (not shown in FIG. 3A) may extend.

Referring now to FIG. 3B, a sectional view of a clamp 5 is provided. As shown in FIG. 3B, the main body 5c of clamp contains a back surface 501 and also an abutting surface 505. As also shown in FIG. 3B, the opening 5b includes conical surfaces 510 and 515 at each side (for convenience, the sides may be considered the "top" and "bottom" sides, respectively, of the clamp 5) the opening 5b. As also shown in FIG. 3B, the tapered end 5d of clamp 5 includes a second abutting portion 550. In addition, opening 5a includes segments or portions 530, 535, 540, and 545. As also shown in FIG. 3B, and in more detail in FIG. 3C, the opening segment 530 is conical in shape and is in direct fluid communication with segment 535. Segment 535, in turn, is in direct fluid communication with segment 540, which in turn is in direct fluid communication with segment 545, which is conical in shape. Segments 530 and 545 have tapered or conical surfaces 520 and 525, respectively. Segment 530 and conical surface 520 are adapted to receive and snugly fit one end of a ferrule 10 (as shown in FIG. 1). We prefer to have clamps 5 made of 2024 T-4 steel, but those skilled in the art will understand that other metals or suitable materials may be used instead.

Figure 4A:
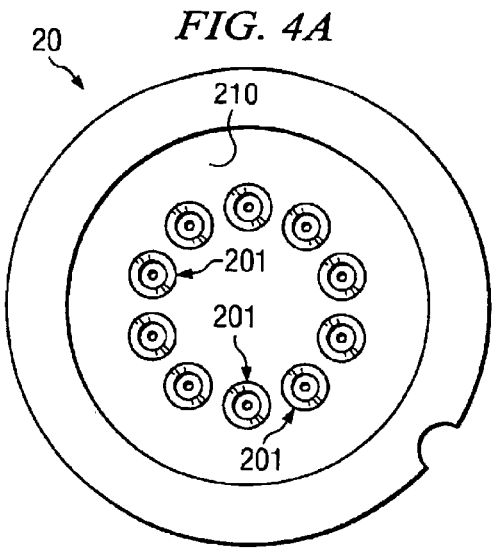
FIG. 4A shows a frontal view of a 10-port stator of a valve in accordance with one embodiment of the present invention.
Figure 4B:
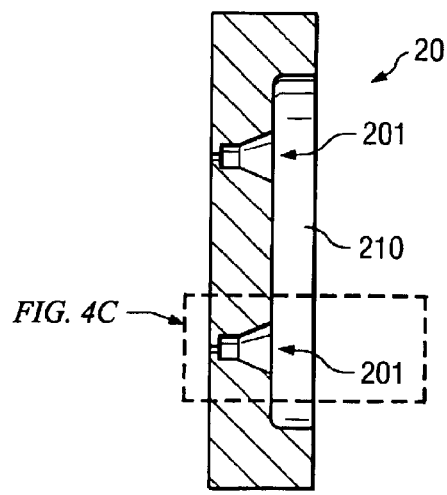
FIG. 4B shows a sectional view of the stator shown in FIG. 4A.
Figure 4C:
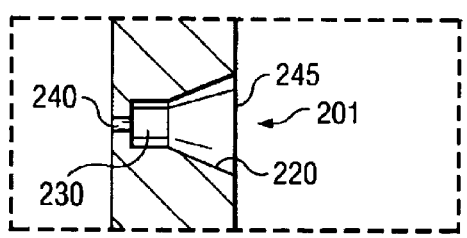
FIG. 4C shows a detailed, fragmentary, sectional view of the stator shown in FIG. 4A.
Figure 4D:
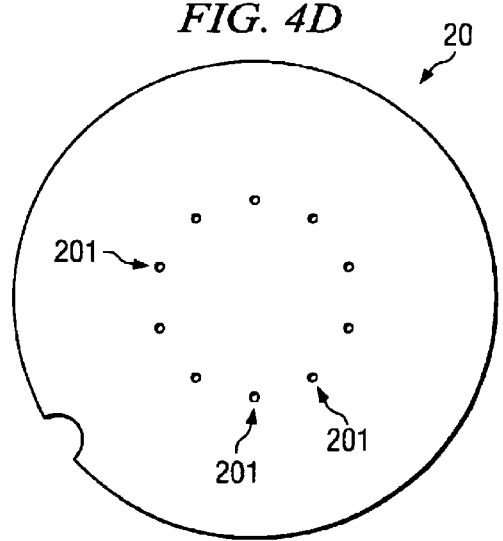
FIG. 4D is a bottom view of the stator 20.
Figure 4E:
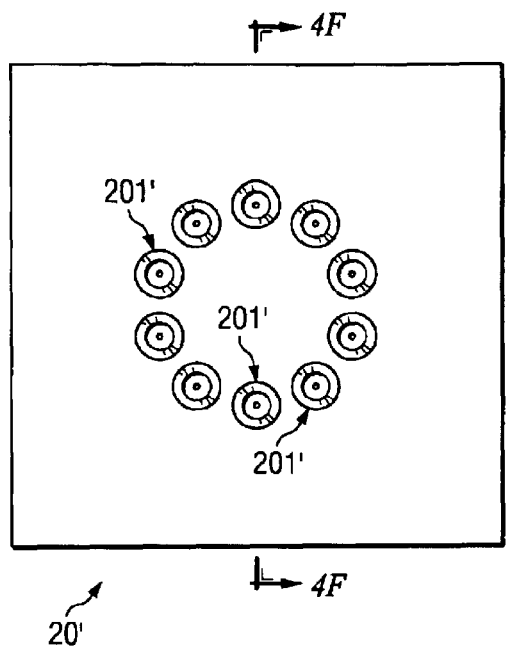
FIG. 4E is a top view of a stator 20' in accordance with an alternative embodiment of the invention.
Figure 4F:
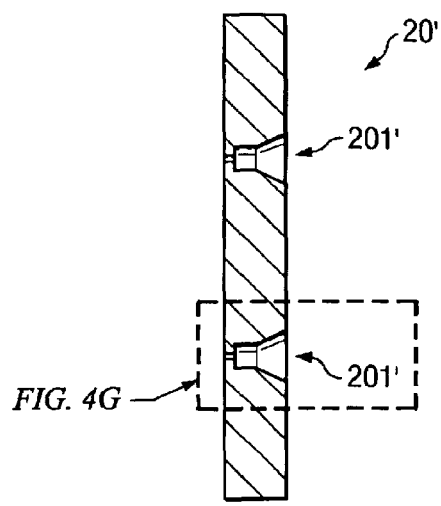
FIG. 4F is a sectional view of stator 20' taken along line 4F—4F.
Figure 4G:
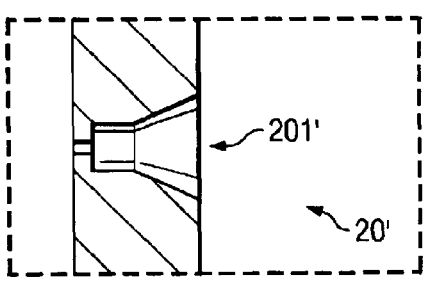
FIG. 4G is a detailed sectional view of a portion of the stator 20'.
Figure 4H:
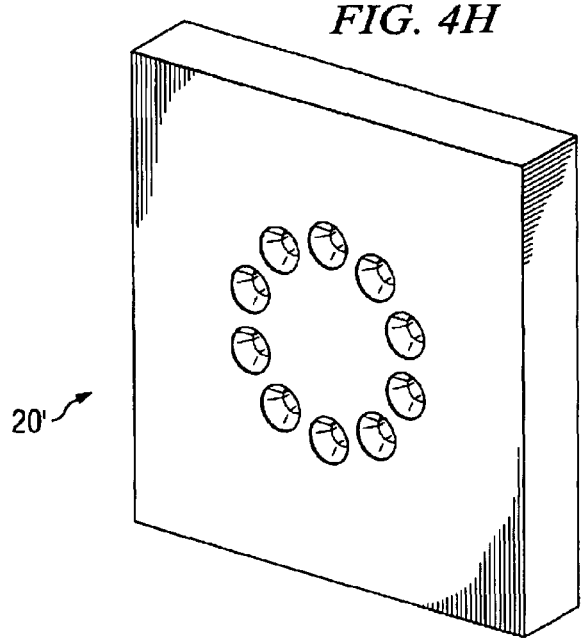
FIG. 4H is a perspective view of the stator 20'.
Figure 4I:
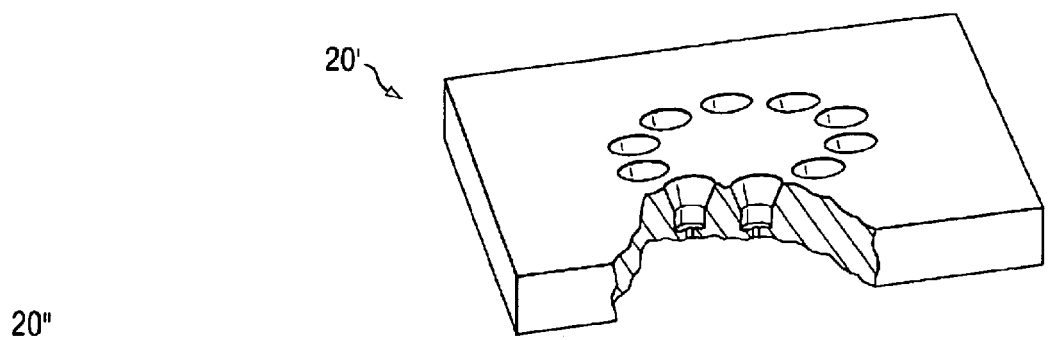
FIG. 4I is another perspective view of the stator 20'.
Figure 4J:
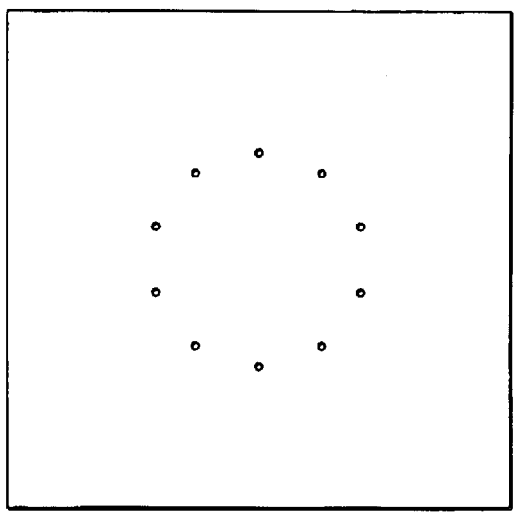
FIG. 4J is a top view of a second alternative embodiment of a stator 20" in accordance with the present invention.
Figure 4K:
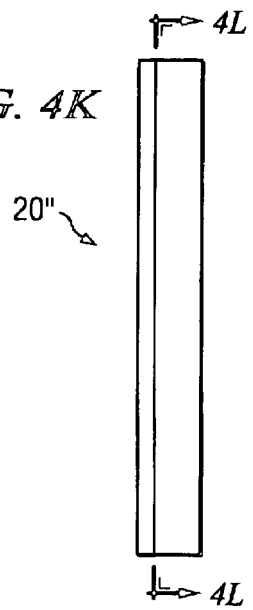
FIG. 4K is a side view of the stator 20".
Figure 4L:
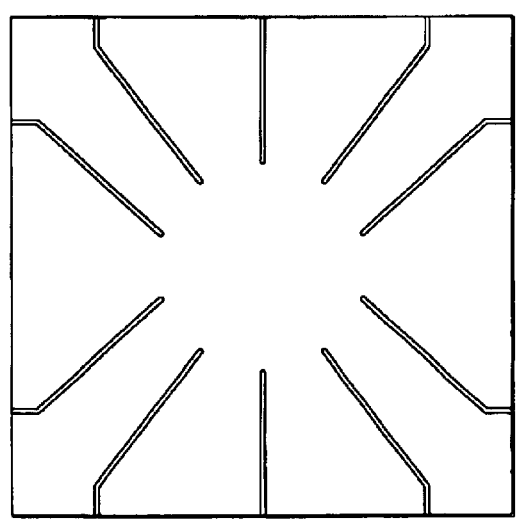
FIG. 4L is a bottom view of a section of stator 20" taken along lines 4L—4L.
Figure 4M:
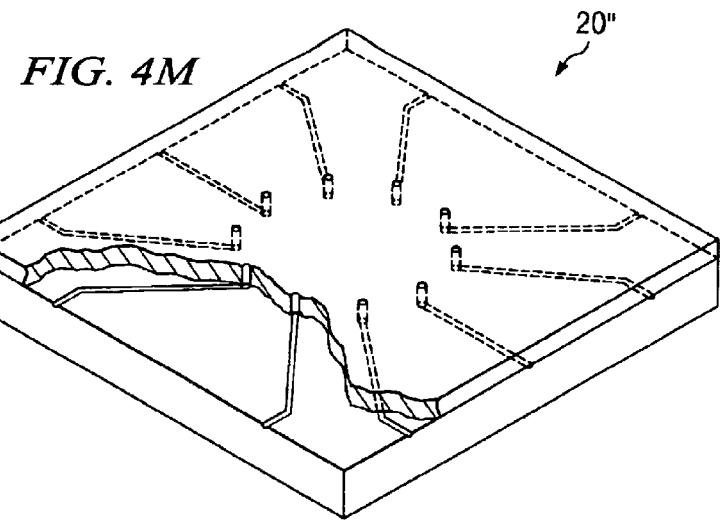
FIG. 4M is a perspective view of the stator 20".

Referring now to FIGS. 4A, 4B, and 4C, additional details regarding the stator 20 of the valve 1 of the present invention are shown. Referring first to FIG. 4A, a frontal view of stator 20 is provided. As shown in FIG. 4A, the interior seat 210 of stator 20 includes ten (10) tapered openings 201. Openings 201 are arranged in a circular pattern on the surface of stator 20. Referring now to FIG. 4B, a sectional view of the stator 20 is provided. As shown in FIG. 4B, a first side of the stator 20 includes a seat 210. The seat 210 is adapted to snugly fit and hold therein at least a portion of the ferrule support 17 (as is shown in FIG. 1). Referring to FIGS. 4B and 4C, the openings 201 are shown in additional detail. As shown in FIGS. 4B and 4C, openings 201 extend through the stator 20. Openings 201 each have segments 240, 230, and 245. As shown in FIG. 4C, segment 245 is tapered and provides a conical surface 220. Segment 230 is in direct fluid communication with segment 245. Segment 240, in turn, is in direct fluid communication with segment 230. Segment 245 and conical surface 220 are adapted to receive and snugly fit a ferrule 10 with a capillary 15 located therein (as is shown in FIG. 1). Segment 230 is adapted to receive and snugly fit a portion of a capillary 15 which may extend from a ferrule. For best results, we prefer that stator 20 be made of zirconia, although other suitable materials may be used.

Referring again to FIG. 1, the capillary tubes 15 emerge from the ferrule through-holes 5a and extend up to the stator 20 through-holes 201 so that the ends of the capillaries 15 are, as noted above, substantially flush with the terminus of a tube pocket. The capillary ends disposed in the tube pockets are naturally in the same relative positions in which the ferrules 10 are arranged. That is, the capillary ends are distributed on the stator 20 evenly around the circumference of a circle in this particular embodiment. Those skilled in the art should understand, however, that the capillary ends need not be located in a circular pattern, but could be arranged in other patterns as desired. For example, in an embodiment where the segments are arranged to be relatively selected or disabled by side-to-side motion (relative to the valve 1) versus rotational movement.

Figure 5A:
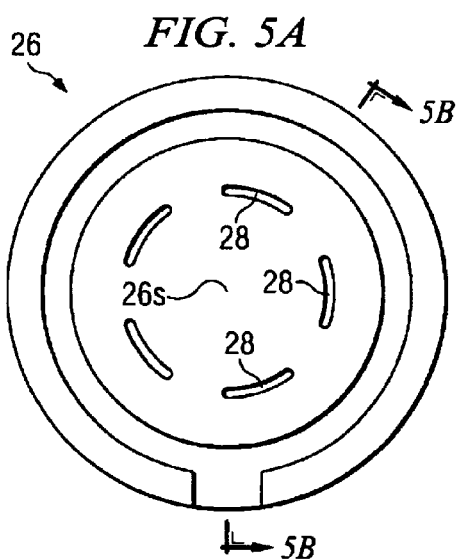
FIG. 5A shows a frontal view of a 10-port rotor of a valve in accordance with one embodiment of the present invention.
Figure 5B:
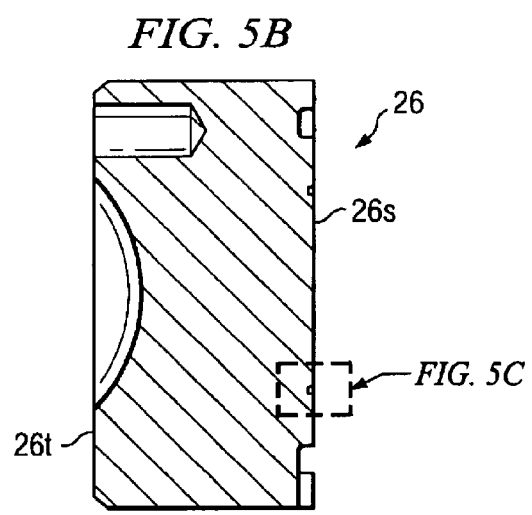
FIG. 5B shows a sectional view of the rotor shown in FIG. 5A.

Referring once more to FIG. 1, the valve 1 shown therein comprises a rotor 26 which abuts the stator 20. The rotor 26 may be of any number of types. Referring to FIGS. 5A and 5B, the rotor 26 shown therein has a grooved stator contact surface 26s and a rotor shaft contact surface 26t. Grooves 28 are formed in the stator contact surface 26s. As shown in FIG. 1, the rotor contact surface 26s abuts one side of the stator 20. Continuing to refer to FIG. 1, the rotor shaft contact surface 26t is connected to a rotor shaft 30 for varying the angle of the rotor 26 with respect to the stator 20. By rotating the rotor surface 26s, the rotor groove(s) 28 may be selectively positioned to establish fluid communication between specific pairs of capillaries 15. Although not shown, those skilled in the art will understand and appreciate that a center capillary can be used and, if so, the grooves 28 can be formed to allow movement of the rotor 26 to selectively provide fluid communication between the center capillary and one or more of the other capillaries. The rotor 26 shown in FIGS. 5A, 5B, and 5C may be used when it is desired to establish fluid communication between various pairs of the capillaries 15. I prefer to use a rotor 26 made of zirconia, but those skilled in the art will understand and appreciate that other suitable materials may be used.

Figure 5C:
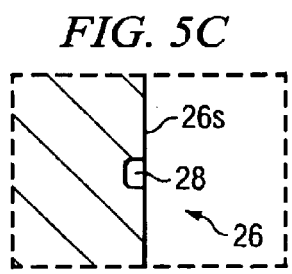
FIG. 5C shows a detailed sectional view of a portion of the rotor shown in FIG. 5B.

While the rotor 26 shown in FIGS. 5A, 5B, and 5C use grooves 28 cut into the rotor surfaces to permit fluid communication between various capillary 15, any type fluid communication channel could be provided on the rotor 26. For example, rather than grooves 28, a channel could be cut in the body of the rotor 26 so that it has one opening at the center of the rotor and another opening lying along the circle circumference. However, to minimize the dead volume of the valve, grooves 28 cut into the surface of the rotor 26 are preferred as rotor fluid communication channels.

The grooves 28 on surface 26s of the rotor 26 can be formed by conventional machining techniques. Alternatively, grooves 28 can be formed by etching of a photolithography mask (photomask). According to this embodiment of the invention, a thin film (or films) is deposited on one face of the surface 26s of the rotor 26 using conventional techniques. The substrate is then coated with a suitable photoresist, is then exposed using the photomask, and is developed with a suitable developer. This process removes the photoresist from those areas of the substrate which correspond to the desired shape and arrangement of grooves 28. The substrate is then subjected to a series of steps which remove the masking material not protected by the photoresist, thus exposing the substrate in these areas. A second series of steps is then use to etch the expose substrate to etch the grooves 28 in the substrate. Because the etching process can be carefully controlled to a very high degree of precision, grooves 28 can be created to match very precise size, volume, shape, or other requirements. Moreover, by carefully controlling the size and shape of the grooves 28, the amount of dead volume can be both minimized and accurately measured, thus giving the operator more information to help design and run accurate analyses, such as by chromatography or mass spectrometry.

After the etching process is completed, the photoresist and masking layers are removed. At this point, the substrate can be coated with a thin conforming film (or films) selected to obtain the desired chemical and/or physical properties of the substrate surface. For example, a thin, inert, chemically resistant coating can be applied to increase the surface hardness, or to add or provide other desired characteristics, such as lesser or greater friction, electrical conductivity or resistance, and/or hydro-affinity. Those skilled in the art will understand and appreciate that, depending on the solvents used, the materials being analyzed, and other various parameters, the ability to select desired chemical and/or physical properties (such as hardness, resistance to corrosion, extremely smooth surfaces, and so forth) will provide many advantages. In addition, a precision saw can be used to cut the substrate into individual pieces for rotor 26, thus allowing a high degree of precision in the alignment and location of grooves 28 on surface 26s of rotor 26.

Figure 6A:
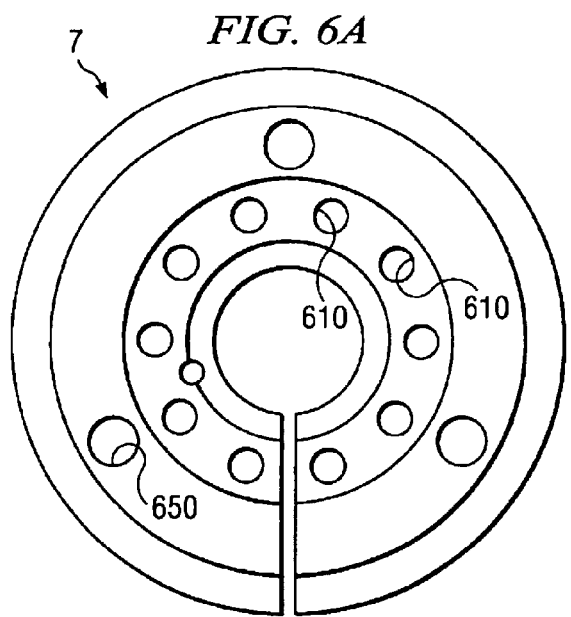
FIG. 6A shows a frontal view of a 10-port stator plate in a valve in accordance with one embodiment of the present invention.
Figure 6B:
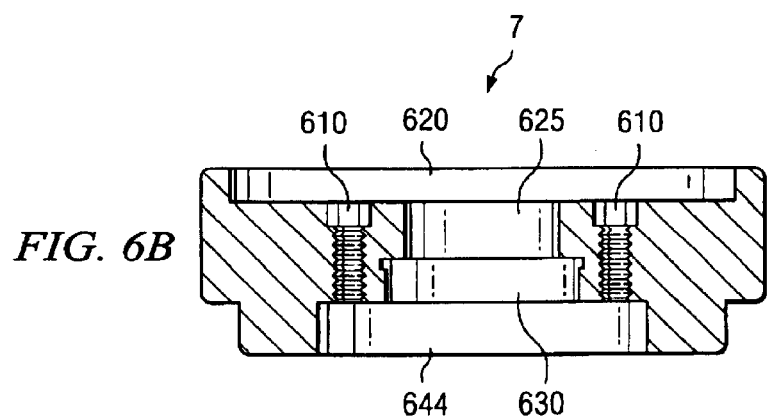
FIG. 6B shows a sectional view of the stator plate shown in FIG. 6A.

Referring now to FIGS. 6A and 6B, additional detail regarding the stator plate 7 is provided. In FIG. 6A, a frontal view of stator plate 7 is provided, while in FIG. 6B a sectional view is provided. As shown in FIG. 6A, the stator plate 7 contains ten (10) openings 610, which are arranged in a circle. The openings 610 are adapted to receive the cap screws 6 which are used to secure the corresponding clamps 5 (as shown in FIG. 1). Stator plate 7 also includes openings 650 for receiving cap screws 2 to firmly (albeit removably) secure stator plate 7 to one end of the main body 110 of valve 1 (as shown in FIG. 1). As shown in FIG. 6A, the stator plate 7 has three (3) openings 650 for receiving cap screws 2. As shown in FIG. 6B, stator plate 7 has central opening segments 620, 625, 630, and 644. In addition, openings 610 have treaded portions for receiving and removably securing cap screws 6 (as shown in FIG. 1). Segments 620 and 625 are adapted for receiving abutting portions of clamps 5, ferrule support 17, and stator 20 (as shown in FIG. 1). Segment 644 is adapted to fit and receive sleeve bearing 11 (as shown in FIG. 1). For best results, we prefer that stator plate 7 be made of 316 stainless steel, although other metals and other suitable materials maybe used instead.

Figure 7:
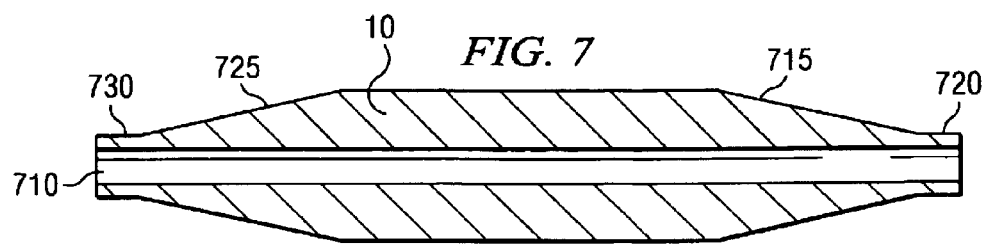
FIG. 7 shows a ferrule in accordance with one embodiment of the present invention.

Referring now to FIG. 7, a cross section of a ferrule 10 is provided. As shown in FIG. 7, the ferrule 10 has a throughhole 710 extending through its length. The opening 710 is adapted to receive a capillary 15. As shown in FIG. 7, ferrule 10 is symmetric and has opposing ends 720 and 730. Referring to FIG. 1, it can be seen that ends 720 and 730 are adapted to fit into openings in the stator 20 and the clamp 5. (Because the ferrule 10 is symmetric, either end 720 or 730 will fit into the respective openings of stator 20 and clamp 5.) As also shown in FIG. 7, ferrule 10 has tapered portions 752 and 715. The tapered portions 725 and 715 are adapted to fit into conical openings in stator 20 and clamp 5 (as shown in FIG. 1). For best results, we prefer to use ferrules 10 made of polyether-ether ketone (PEEK), which is commercially available.

Figure 8A:
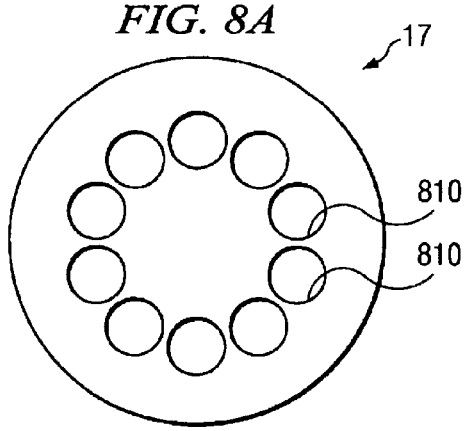
FIG. 8A shows a frontal view of a ferrule support in a valve in accordance with one embodiment of the present invention.
Figure 8B:
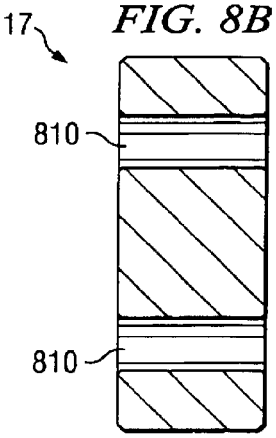
FIG. 8B shows a sectional view of the ferrule support shown in FIG. 8A.
Figure 10A:
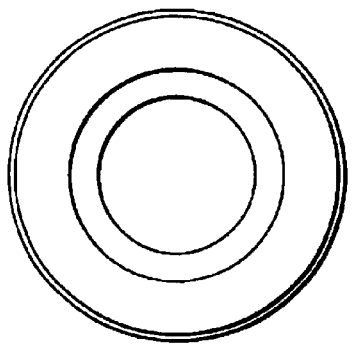
FIGS. 10A, 10B and 10C are, respectively, a frontal view, sectional view, and sectional view along line 10A—10A, of an adjustment nut in a valve of one embodiment of the present invention.
Figure 10B:
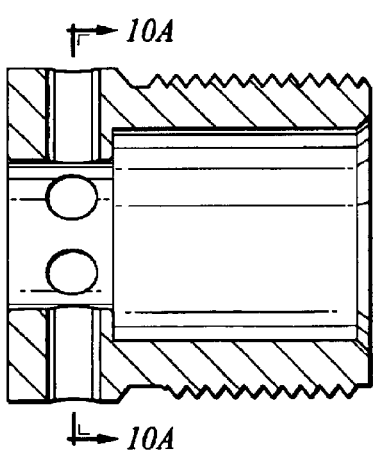
Figure 10C:
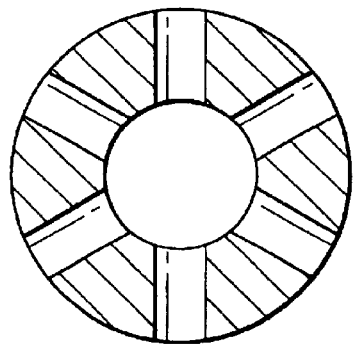
Figure 11A:
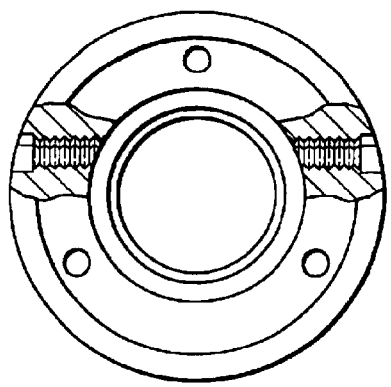
FIGS. 11A, 11B, and 11C are a frontal view, sectional view, and rear view, respectively, of the main body of a valve of one embodiment of the present invention.
Figure 11B:
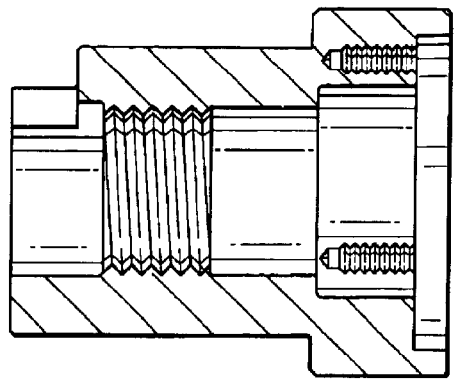
Figure 11C:
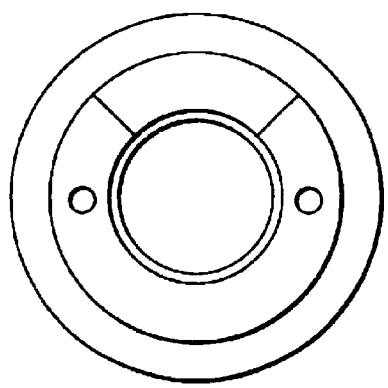
Figure 12A:
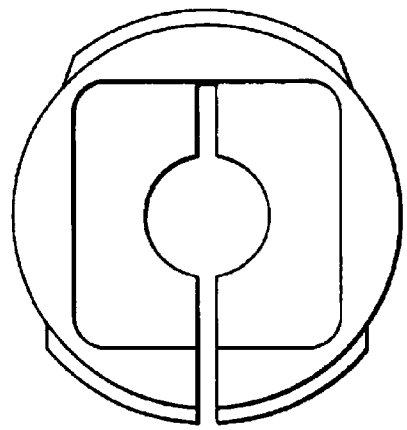
FIGS. 12A, 12B, and 12C are a frontal view, sectional view, and rear view, respectively, of the rotor mount of a valve of one embodiment of the present invention.
Figure 12B:
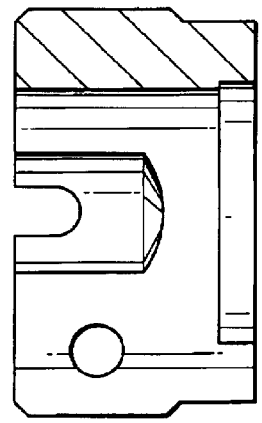
Figure 12C:
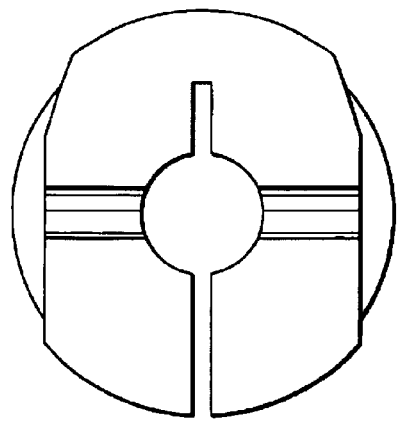
Figure 13A:
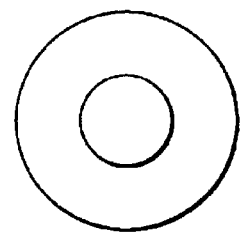
FIGS. 13A and 13B are a frontal view and a side view, respectively, of a drive shaft of a valve of one embodiment of the present invention.
Figure 13B:
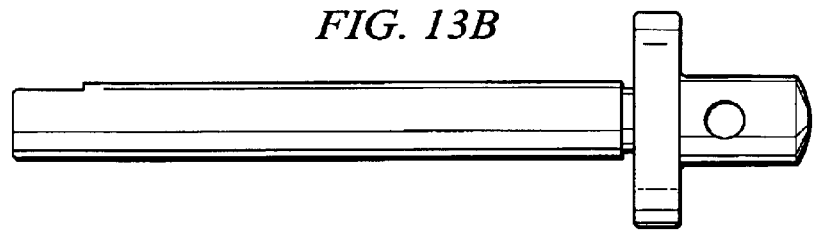
Figure 14A:
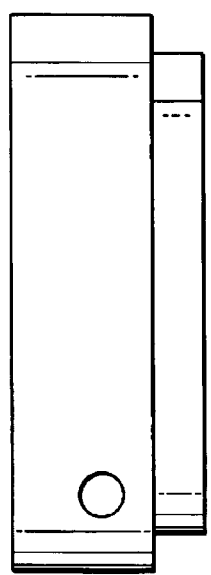
FIGS. 14A and 14B are side and frontal views, respectively, of an alternative stator plate of a valve in accordance with one embodiment of the present invention.
Figure 14B:
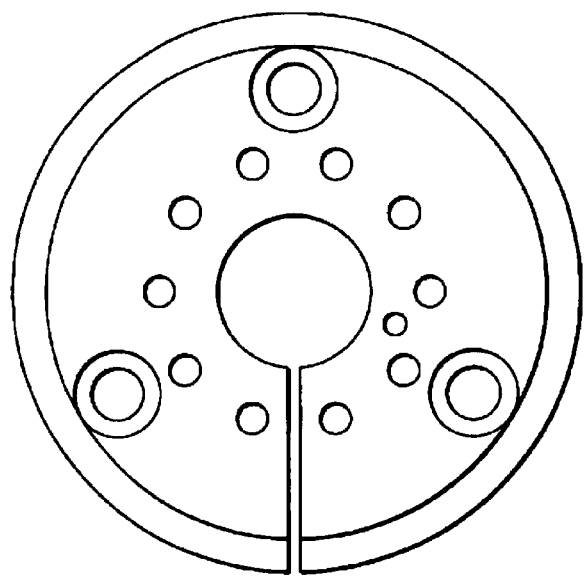

Referring now to FIGS. 8A and 8B, the ferrule support 17 is shown in additional detail. As shown in FIGS. 8A and 8B, the ferrule support 17 has ten (10) openings 810, which are generally located in a circle. The openings 810 are adapted to receive and snugly fit ferrules 10 (as shown in FIG. 1). We prefer to have a ferrule support 17 made of PEEK, but any suitable material may be used.

Returning to FIG. 1, rotor shaft 30 is connected to rotor surface 26t and is supported by bearing bushing 32 and roller thrust bearing 34. A spring 36 is used to bias the rotor shaft and rotor 26 toward the stator 20. A rotor driver pin 40 engages the rotor, and a handle 42 is used for operating the rotor if manual rotation thereof is desired. Obviously, any number of automatic means for rotating the rotor could be connected to the rotor shaft.

The various components of valve 1 as described above may be fabricated form any suitable material, including thermoset materials and thermoplastics. Polyether-ether ketone (PEEK) is a particularly suitable thermoplastic material for fabricating the ferrules of the invention. The rotor and stator of the inventive valve may be fabricated from any suitable material, for example, metal, plastic materials, ceramic materials, or zirconia. In a preferred embodiment, the rotor and stator are ceramic or zirconia.

The valve of the instant invention may be fabricated to any useful size. However, the inventive valve is particularly useful in micro applications, in particular those utilizing fluid flow rates of 0.5 ml/min or less. For example, in the preferred embodiment shown above, the valve 1 is able to selectively connect ten (10) capillaries 15 with a port to port distance of 2 mm arranged in a circle with a diameter of 6 mm. The valve 1 of the present invention thus minimizes dead volume while providing a great deal of flexibility and ease of use to an operator because each capillary 15 can be connected or disconnected separately; the cap screws 6 (arranged in a larger circle than capillaries 15) can be easily tightened or loosened by an operator. Those skilled in the art will understand and appreciate that more or less than ten (10) ports may be used, and the size of the ports may be greater or less than 2 mm in diameter. The valve 1 of the present invention will be of advantage in the field of capillary chromatography and mass spectrometry. As used herein, the terms "capillary chromatographic system" and "capillary chromatography" shall be understood to refer to systems used for chromatographic analyses or mass spectrometry analyses performed thereon, and the like, which employ(s) one or more capillary columns. As used herein, "capillary column" means a capillary (capillary tube) having an outside diameter from about 100 to about 1600 microns. It will be understood that the capillaries which may be connected to the inventive valve need not be "capillary columns," although they may be. For example, some of the capillaries may be shorter capillaries which are used to feed or transfer fluids to a capillary column. Those skilled in the art will understand that the terms "chromatographic analysis" and "mass spectrometry analysis," and the like refer not only to the separation or partial separation of mixtures into their individual components, but also to methods in which a single, pure material is analyzed. In the latter situation, it may technically be the case that no "separation" occurs, because only a single, pure component is present. Further, as noted above a distinction is sometimes made between analytic methods which are performed for analytical purposes and those which are performed for preparative purposes. However, for convenience, the terms "chromatographic analysis" and "mass spectrometry analysis," and the like, as used herein will be understood to include separations and methods which are conducted for both analytical and preparative purposes.

Capillary chromatography has long been known for extremely high resolution, and it can be carried out using both gas and liquid mobile phases. In this sense the term "fluid" will be understood, as it normally is, to include both liquids and gases. The valve of the present invention is also useful in high pressure liquid chromatographic (HPLC) applications, including capillary HPLC. Thus, one embodiment of the invention is a capillary chromatographic system, including gas chromatographs and liquid chromatographs, comprising the valve of the invention.

In another embodiment of the invention, the capillary 15 are fused silica capillaries having an outside diameter of about 365 microns. In other embodiments, the outside diameter of the capillaries is between about 100 and 500 microns, and preferably between about 250 and 400 microns.

In yet another embodiment, the present invention is a method for carrying out a chromatographic mass spectrometry analysis, comprising: a) inserting one end of a capillary into an opening of a ferrule and the other end of the capillary through a clamp; b) placing a stator in contact with at least one of said ferrules, said stator having a stator front side and a stator flat surface opposite said front side, said stator front side having a plurality of impressions into which some or all of said ferrules are received, each of said impressions opening to a tube pocket, each of said impressions also having a stator through-hole opening onto said stator flat surface; c) disposing a plurality of capillary tubes through said ferrules into said tube pockets; d) applying pressure to said one or more ferrules; e) placing in contact with said stator a rotor comprising a stator-contact surface and a fluid communication channel such that said stator-contact surface abuts said stator flat surface and is rotatable about an axis to establish fluid communication between selected pairs of capillaries through said fluid communication channel; f) placing one or more of said capillaries in fluid communication with a capillary column; g) rotating said rotor to establish fluid communication between said capillary column and one or more of said capillaries; and h) passing a fluid through one or more of said capillaries and into said capillary column. In yet a further embodiment, the present invention is an automated method or automated chromatographic system or mass spectrometry for carrying out a chromatographic or mass spectrometry analysis using the valve of the invention.

In still another embodiment, the present invention is a method for connecting capillaries to a chromatographic or mass spectrometry system, the method comprising: a) providing a plurality of ferrules, each of said ferrules having a ferrule through-hole; b) disposing a plurality of capillary tubes through said ferrule through-holes; c) inserting the other end of each capillary through an opening in a clamp; and d) providing a plurality of impressions into which said some or all of ferrules are received, each of said impressions having a tube pocket into which one of said capillary tubes extends; and e) applying pressure to said one or more ferrule clusters.

Figure 15:
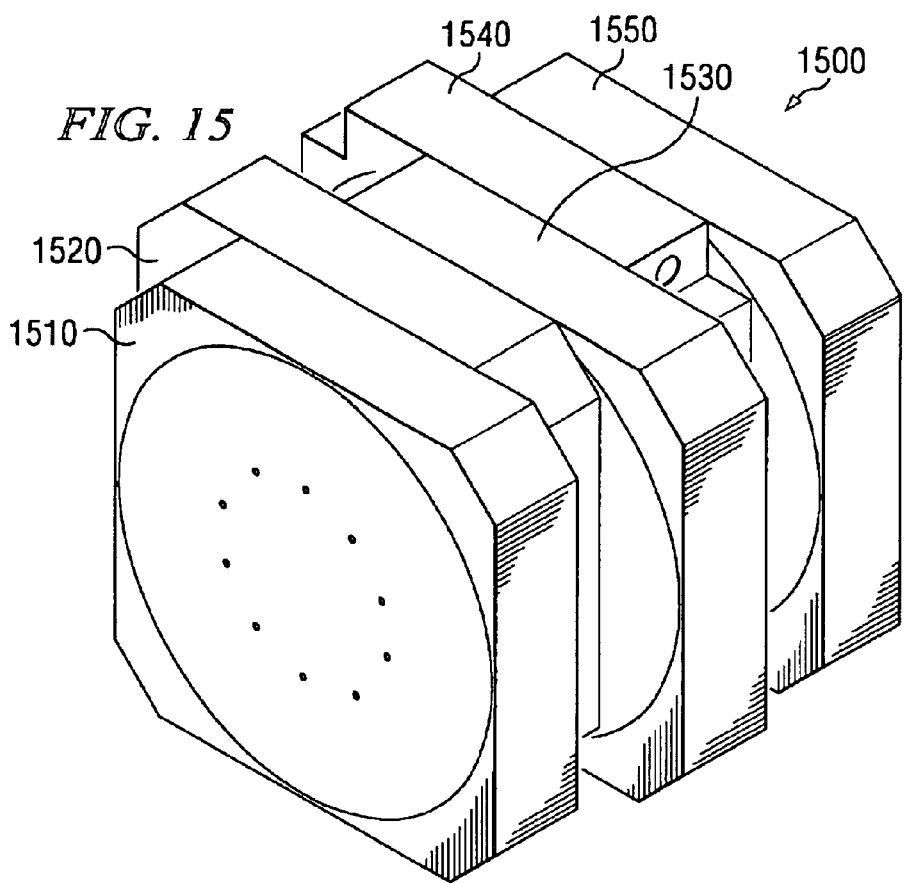
FIG. 15 shows the "stacked" configuration of a series of elements of a valve in accordance with an embodiment of the invention.

Referring now to FIG. 15, a series of "stacked" discrete elements useful for analytical chemistry are shown. In FIG. 15, the series 1500 of elements 1510, 1520, 1530, 1540, and 1550 is shown. Although the series 1500 is shown and described as having five discrete elements 1510, 1520, 1530, 1540, and 1550, it will be appreciated that more or less such elements can be used in accordance with the invention. In addition, it will be appreciated that, although the series 1500 is shown and described with respect to elements 1510, 1520, 1530, 1540, and 1550, different elements than those shown can be used in accordance with the invention.

Still referring to FIG. 15, the series 1500 includes a first element 1510, which is a variable sample loop element (described in more detail below and shown in FIG. 15C). The second element 1520 is a mixer element (described in more detail below and shown in FIG. 15D). The third element 1530 includes a column element (as well as a sample loop 1534a and a flow cell loop 1536c, as described below and shown in FIG. 15E). The fourth element 1540 of series 1500 of FIG. 15 includes a detector element 1540 (described below and shown in FIG. 15F). The fifth element 1550 of the series 1500 include ports for input or output of the liquid or gas samples.

As shown in FIG. 15, each of the elements 1510, 1520, 1530, 1540, and 1550 of the series 1500 is located in an offset position from the adjacent element, with elements 1520 and 1540 aligned with one another. Similarly, elements 1510, 1530, and 1550 are aligned with one another, yet offset from each of elements 1520 and 1540. This arrangement allows the elements 1510, 1520, 1530, 1540, and 1550 to be selectively positioned relative to one another to selectively interconnect the ports allowing fluid communication provided by the elements 1510, 1520, 1530, 1540, and 1550 of the series 1500.

Figure 15A:
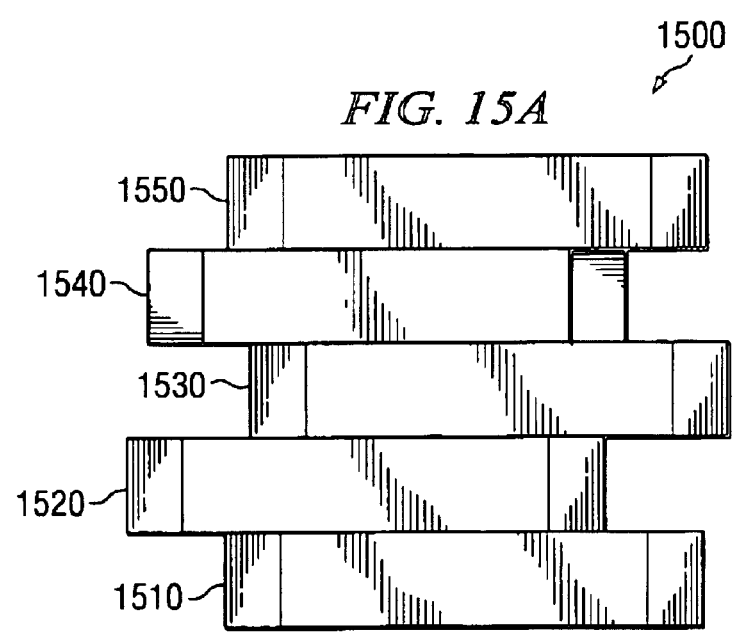
FIG. 15A shows a "top" view of the elements shown in FIG. 15A.

Referring now to FIG. 15A, the series 1500 of elements 1510, 1520, 1530, 1540, and 1550 is shown from a "top" view. (It will be appreciated that the valve of the present invention can actually be used in any orientation in space, so the reference to the "top" view of FIG. 15A is overly simplistic and used only for convenience of the discussion.) As shown in FIG. 15A, the series 1500 includes the elements 1510, 1520, 1530, 1540, and 1550 in the "stacked" configuration. As can be seen in FIG. 15A, the elements 1520 and 1540 are positioned with their center lines to the left of the center line of the entire series 1500, while each of the elements 1510, 1530, and 1550 are positioned so that each of their respective center lines is to the right of the center line of the entire series 1500. It can also be seen that elements 1520 and 1540 need not be aligned with one another, and that elements 1510, 1530, and 1550 also need not be aligned with one another.

Figure 15B:
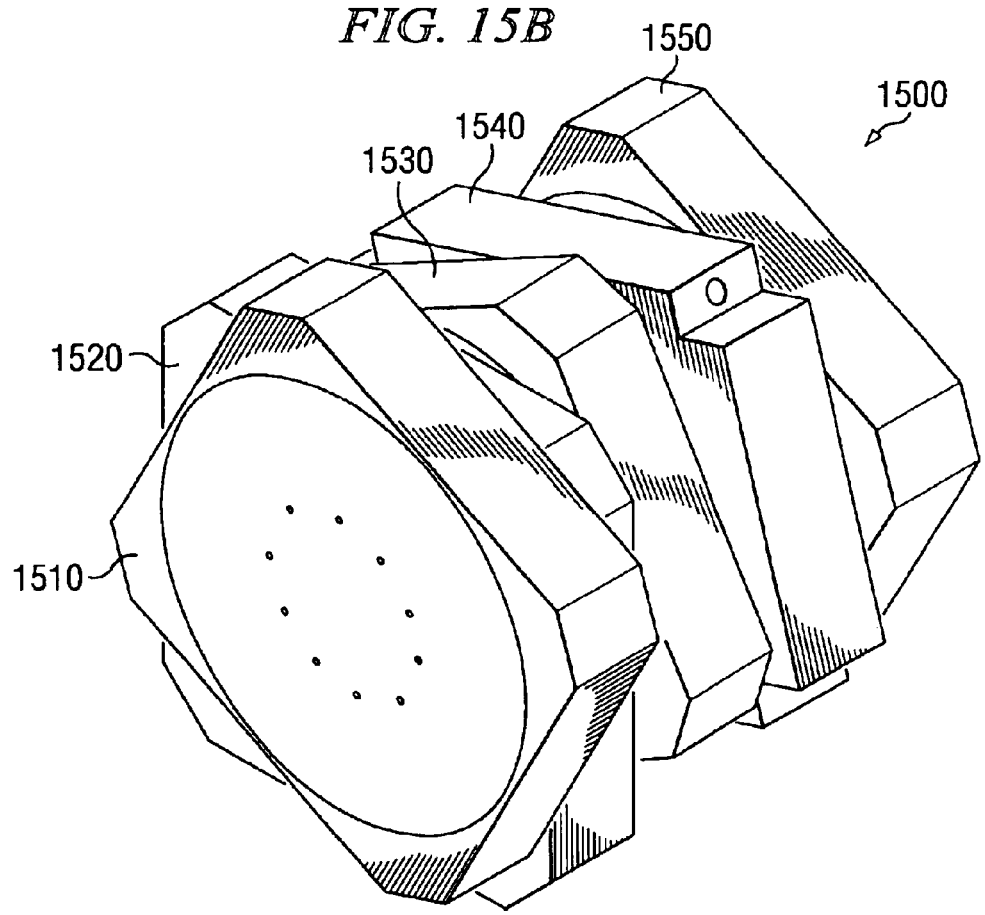
FIG. 15B shows an alternative embodiment of the series of elements of a valve in accordance with an embodiment of the invention.

Referring to FIGS. 15A and 15B, it will be appreciated that one or more of the various elements 1510, 1520, 1530, 1540, and/or 1550 in a stacked element valve system can be actuated relative to the others. Movement of each of the elements 1510, 1520, 1530, 1540 and/or 1550 component can be accomplished in various ways. For example, the use of individual motors (not shown) coupled to individual elements via a mechanical drive system (not shown) is one approach. Such systems are conventional for use with a conventional rotor with respect to conventional selection valves for LC. One advantage of this approach is that such motors (not shown) can be automatically controlled based on feedback loops. Feedback can be provided by transducers or sensors (not shown) measuring/sensing parameters, such as pressure, relative pressure, position, or relative position, temperature flow rates, and the like, as well as the relative positions of one or more of elements 1510, 1520, 1530, 1540, and/or 1550. The motors (not shown) can be controlled by a computer (not shown) which is preprogrammed to align and selectively position one or more of the elements 1510, 1520, 1530, 1540, and/or 1550 as desired. Thus, the computer (not shown) can selectively position elements 1510 and 1520, for example, in response to a signal from a sensor (not shown) that a predetermined condition has been met (e.g., a particular pressure, elapsed time, or the like); the computer (not shown) is programmed to then send appropriate signals to the motors (not shown) coupled to elements 1510 and 1520 to move them as needed into the desired positions. Actuation and selection positioning of any given element can be made for the purpose of making a minimal volume fluidic connection between one or more elements.

Still referring to FIG. 15A, it can be seen that an operator can selectively position the various elements 1510, 1520, 1530, 1540, and 1550 so that any desired combination of such elements is selected. For example, the operator can slide the element 1520 to the right of the position shown in FIG. 15A so that elements 1510 and 1520 are aligned with one another. Similarly, the operator can also then slide the element 1530 to the left of the position shown in FIG. 15A so that elements 1510, 1520, and 1530 are aligned with one another. By selectively positioning and aligning the elements 1510, 1520, 1530, 1540, and 1550, the operator can select the various features of the various elements 1510, 1520, 1530, 1540, and 1550 for performing the analysis of gas or liquid samples which flow through the valve provided in accordance with the present invention.

Referring now to FIG. 15B, an alternative embodiment is shown. In FIG. 15B, the series 1500 of elements 1510, 1520, 1530, 1540, and 1550 is also shown in a "stacked" configuration. However, in FIG. 15B, the various elements 1510, 1520, 1530, 1540, and 1550 are aligned with one another, so that each of the elements 1510, 1520, 1530, 1540, and 1550 can be selectively positioned by an operator by selectively rotating one or more of the elements 1510, 1520, 1530, 1540, 1550 as desired to obtain the selected alignment of the various elements 1510, 1520, 1530, 1540, and 1550. Generally, the operator can selectively rotate the desired elements 1510, 1520, 1530, 1540, and/or 1550 so that the respective elements either engage, isolate, or entirely bypass the functions and features of the elements in the series.

Still referring to FIG. 15B, it will be appreciated that elements 1510, 1520, 1530, 1540 and 1550 are biased so that they are held tightly against adjacent elements and thus sealed by compression force. Each of the elements is secured, restrained and/or driven within the body of valve 1 through use of a "carrier" 1575 which engages the external edges of each element. An example of a carrier 1575 is shown in FIGS. 17–17D and described in more detail below. In addition to use of the carriers 1575, the elements 1510 and 1550 (which, as shown in FIGS. 15A and 15B, are at the two ends of the stack of elements 1510, 1520, 1530, 1540, and 1550) can be movably held within the body of valve 1 via the use of special carriers 1585 (not shown) which are adapted for allowing selective fluidic connection to each of the elements 1510, 1520, 1530, 1540, and 1550. The carriers 1575 and 1585 may be push/pull in actuation, or rotated via mechanical drive to separate motors or teamed via transmission to a shared motor (not shown).

Figure 15C:
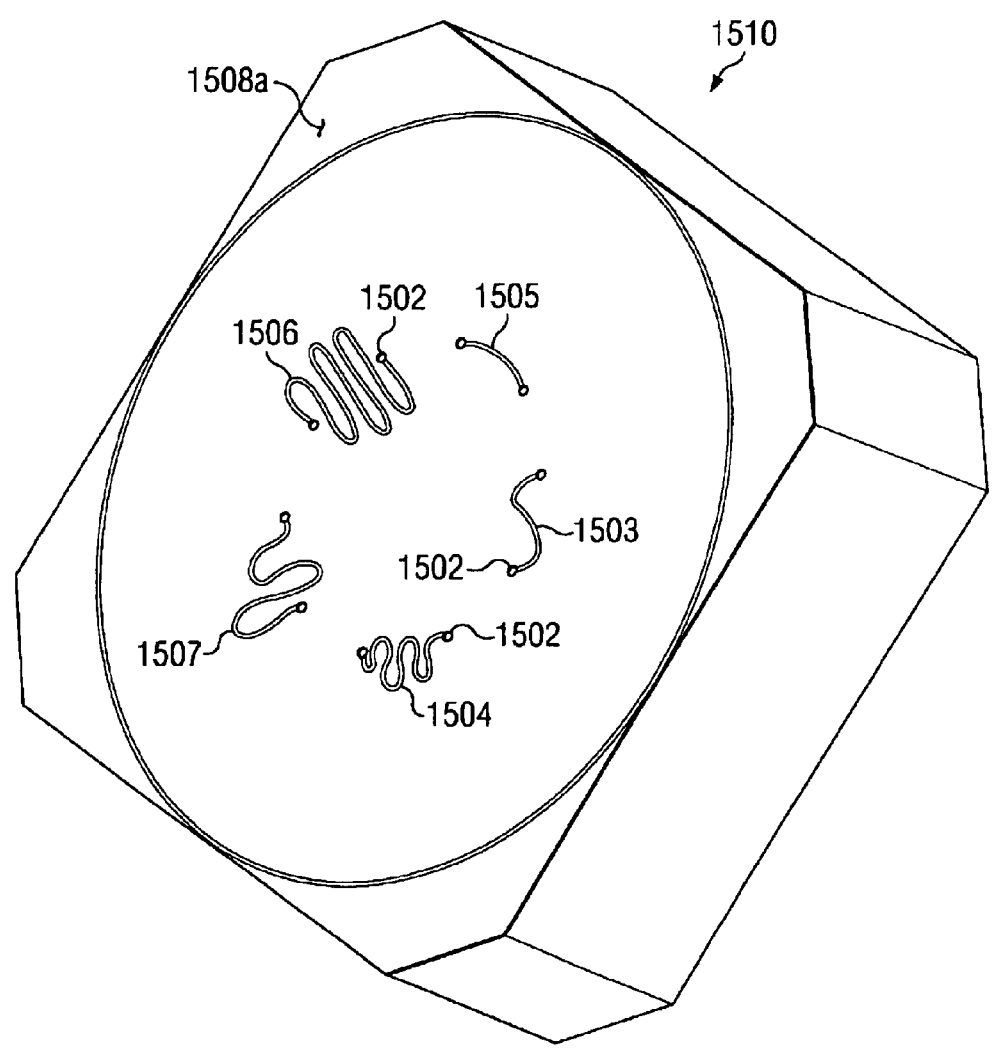
FIG. 15C shows one element of an embodiment of the invention.

Referring now to FIG. 15C, a more detailed view of the element 1510 is shown. As shown in FIG. 15C, element 1510 can be described as a varietal sample loop. The element 1510 includes five different sample loops 1503, 1504, 1505, 1506, and 1507 of varying sizes. The varying sizes thus accommodate samples of different volumes, each of which can be relatively precisely determined based on the volumes of the varying loops 1503, 1504, 1505, 1506, and 1507. As shown in FIG. 15C, a top surface 1508a of the element 1510 has the sample loops formed thereon. As with the grooves 28 of the valve 1 described above, the loops 1503, 1504, 1505, 1506 and 1507 can be formed by etching the face 1508a of the element 1510. Such a process allows for strict control over the size and volume of the resulting loops 1503, 1504, 1505, 1506, and 1507. It will be appreciated that the element 1510 is of an appropriate size and shape so that it fits within the body of the valve, yet can be moved either from side to side or can be rotated by an operator so that the element 1510 can be selectively positioned with respect to the other elements of the series 1500.

Figure 15D:
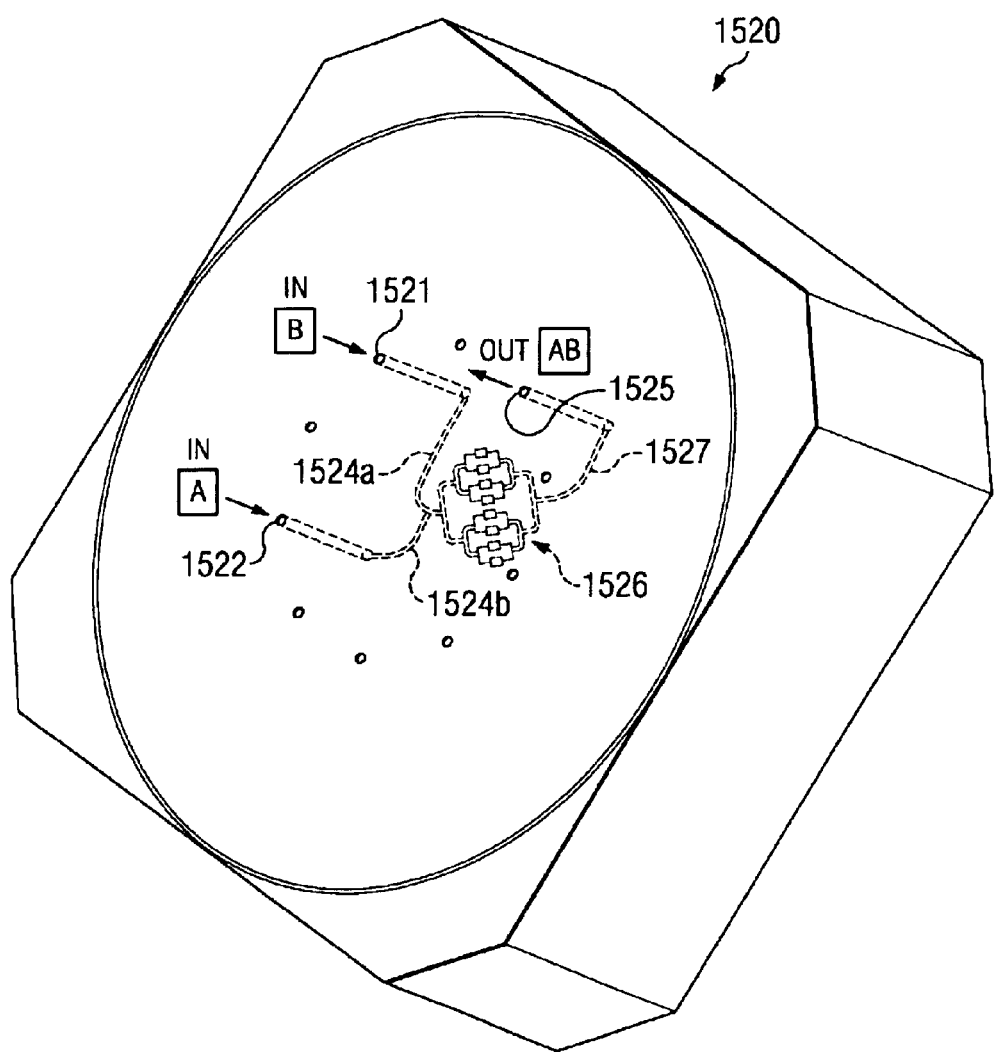
FIG. 15D shows one element of an embodiment of the invention.

Now referring to FIG. 15D, element 1520 is shown in more detail. Element 1520 comprises a mixer element. As shown in FIG. 15D, the element 1520 has a series of ten ports located substantially in a circular pattern. As shown in FIG. 15D, ports 1521 and 1522 provide fluid communication via two streams 1524a and 1524b to a common mixing portion 1526 of the element 1520. The mixing element 1526 takes two incoming streams, separates each into multiple smaller streams, then combines the various separated streams back into a single stream, now blended, which is then conducted via stream 1527 to an output from port 1525 of element 1520. As with the sample loops of element 1510, the streams 1524*a*, 1524*b*, and 1527 of element 1520 can be provided as grooves on one side of the element 1520. Such grooves can be formed to have relatively precise measurements and volumes, thus allowing the operator greater control and precision in analyzing samples.

In FIG. 15E, element 1530 is shown in more detail. In FIG. 15E, the element 1530 comprises a column 1533. The column 1533 is essentially a "loop" formed in element 1530 between ports 1531 and 1535, which provide fluid communication into and out of the column 1533 of element 1530. It will be appreciated that the column 1533 can be pre-packed with any one of a number of packing materials, depending on the type of separation which is to be performed by the column 1533. Such packing materials (not shown) are conventional in the art and are commercially available from a variety of sources. For example, suitable packing materials can be obtained from the Grace Vydac company of Hisperia, Calif. Examples of suitable packing materials include the C-18 and C4 condition silica and silica gels from such company.

Still referring to FIG. 15E, the column 1533 of the element 1530 is located within close proximity of a heating element 1537. In FIG. 15E, the portion 1537*a* of the heating element 1537 extends along and is within close proximity of the column 1533. The heating element 1537*a* can be used to heat the column 1533 to a desired temperature level or cool to a desired temperature as well to provide for a more effective and efficient separation performance by the column 1533. We prefer to use a resistance heating element 1537 which can be heated by simply applying an electric potential to the heating element 1537. By selectively controlling the electrical resistance of the heating element 1537 and the voltage applied to the heating element 1537, the heating of the column 1533 and its temperature can be selectively controlled. It should be noted that a cooling element, which would likely appear different from the heating element 1537, is not shown.

Still referring to FIG. 15E, it can be seen that element 1530 also includes a loop 1534*a*, which is formed between ports 1534 and 1534*b* located on the same surface of element 1530 as are ports 1531 and 1535. In addition, the element 1530 includes a detector loop 1536*c*, which is in fluid communication with ports 1536*a* and 1536*b*. The detector loop 1536*c* is located within the element 1530 and positioned so that the loop 1536*c* is between two openings 1536*d*' and 153*d*'' of the element 1530. As shown in FIG. 15E, a first fiber optic element 1536*e*' is positioned within the first opening 1536*d*', while a second fiber optic element 1536*e*'' is positioned within the second opening 1536*e*'''. Thus, the fiber optic elements can transmit optical information to and from the sample loop 1536*e* of element 1530. By transmitting light, for example, to the sample loop 1536*c* via the first fiber optic element 1536*e*', and then analyzing the resulting information obtained from element 1530 and the sample contained in sample loop 1536*c* via the second fiber optic element 1536*e*'', the operator can determine certain properties and characteristics of the sample within the sample loop 1536*c*.

It will be appreciated that element 1530, as shown in detail in FIG. 15E, provides multiple different features and functions which are useful in analytical chemistry. Although element 1530 has been shown and described as containing a sample loop 1534*a*, a column 1533, and a detector loop 1536*c*, it will be appreciated that element 1530 could include different features or functions, and could contain less, or more features or functions, in accordance with the present invention.

Figure 15F:
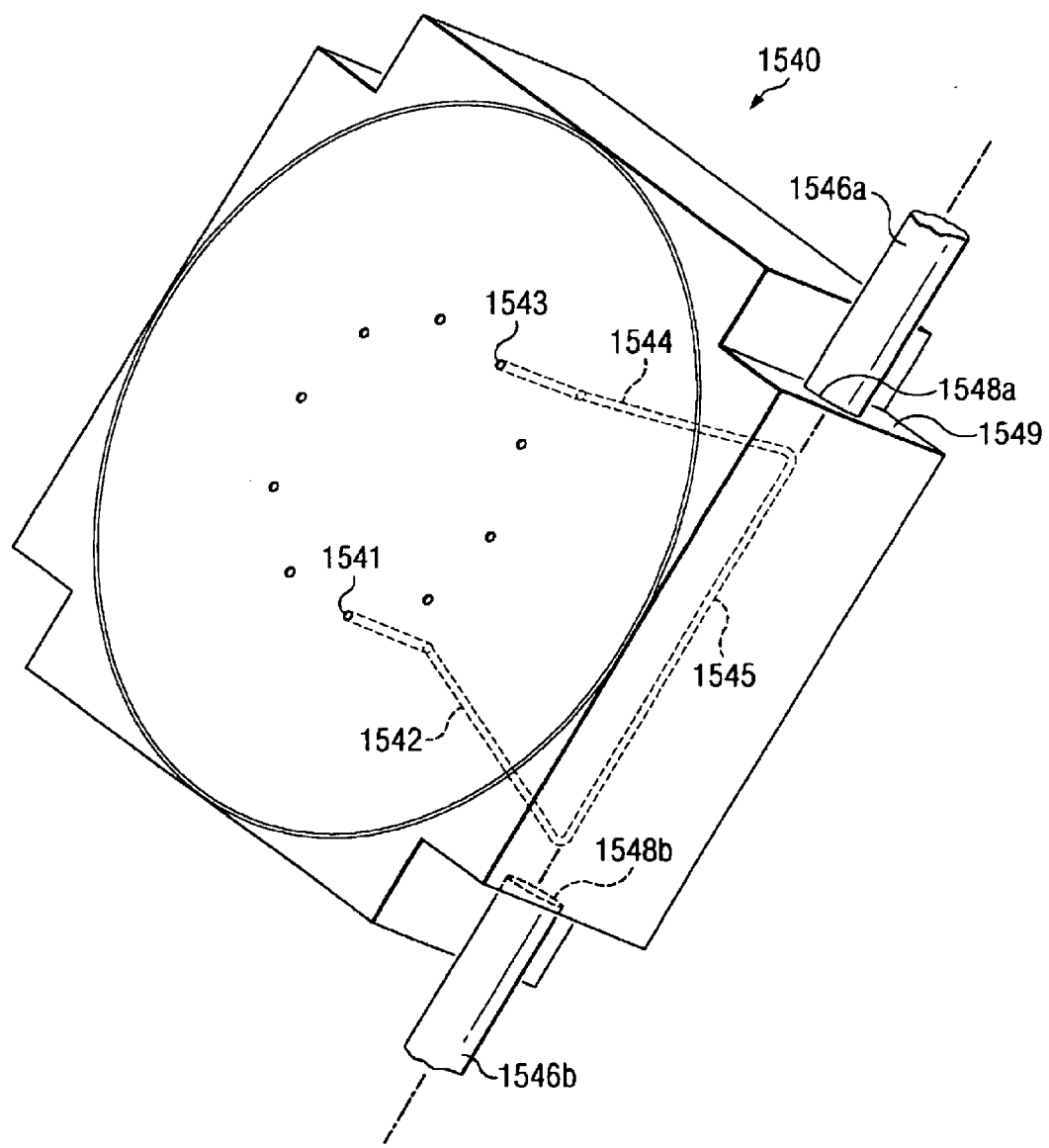
FIG. 15F shows one element of an embodiment of the invention.

Referring now to FIG. 15F, element 1540 is shown in more detail. As shown in FIG. 1540, the element 1540 includes ports 1543 and 1541, which are in fluid communication with a loop 1545. The loop 1545, in turn, is positioned within element 1540 so that portions of first and second fiber optic elements 1546*a* and 1546*b* can be positioned within openings 1548*a* and 1548*b*, respectively, of the portion 1549 of element 1540. The first and second fiber optic elements 1546*a* and 1546*b* can be used by an operator to obtain information regarding the sample within the sample loop 1545 of the element 1540.

Figure 15G:
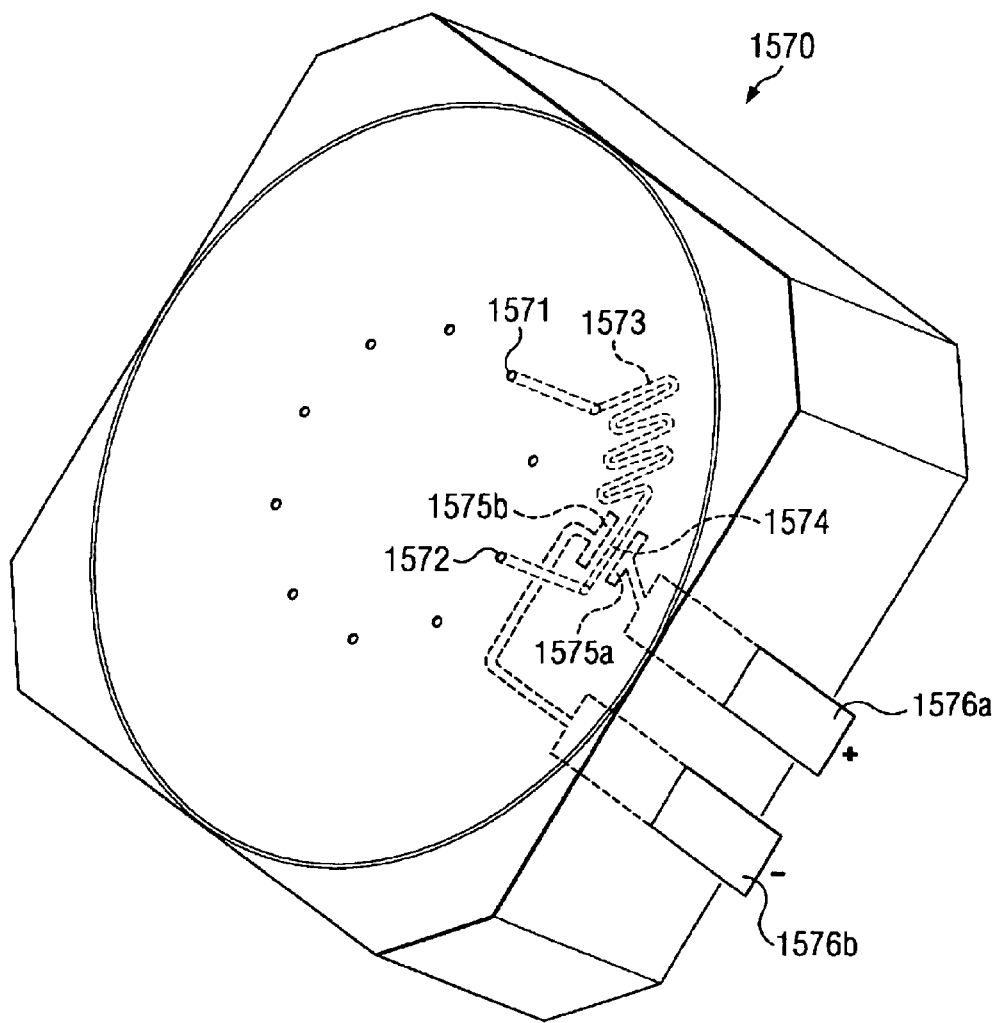
FIG. 15G shows one element of an embodiment of the invention.

Referring now to FIG. 15G, an alternative element 1570 is shown in detail. As noted above, the series 1500 may include elements other than those shown and described as elements 1510, 1520, 1530, 1540, and 1550. In FIG. 15G, element 1570 includes an electrical flow sensor loop 1574. As shown in FIG. 15G, ports 1571 and 1572 provide fluid communication via the sensor loop 1574. After passing into port 1571, the sample passes through a sample loop 1573 (which, it will be appreciated, can be of a desired size and volume), and then through the sensor loop 1574, finally passing out of port 1572. (Of course, the direction of flow can be reversed, if so desired by the operator.) The sensor loop 1574 passes between two electrical sensors 1575*a* and 1575*b*, which are positioned and located on opposing sides of the sensor loop 1574. An electrical potential can be applied to the sensors 1575*a* and 1575*b* via application of an electric voltage across terminals 1576*a* and 1576*b*, respectively. By selectively applying an electric voltage across the sensor loop 1574, the operator can determine certain electrical properties and characteristics of the sample within the sensor loop 1574. Flow rate can be measured by transmitting or otherwise providing the flow rate information to a controller which actuates one element relative to a mate or mates—causing or relieving constriction (aperture change) to provide active flow rate control. Further, it will be appreciated by those skilled in the art that valve 1 can be adapted to changes in applied flow rate, or pressure via user input control program parameters.

Figure 15H:
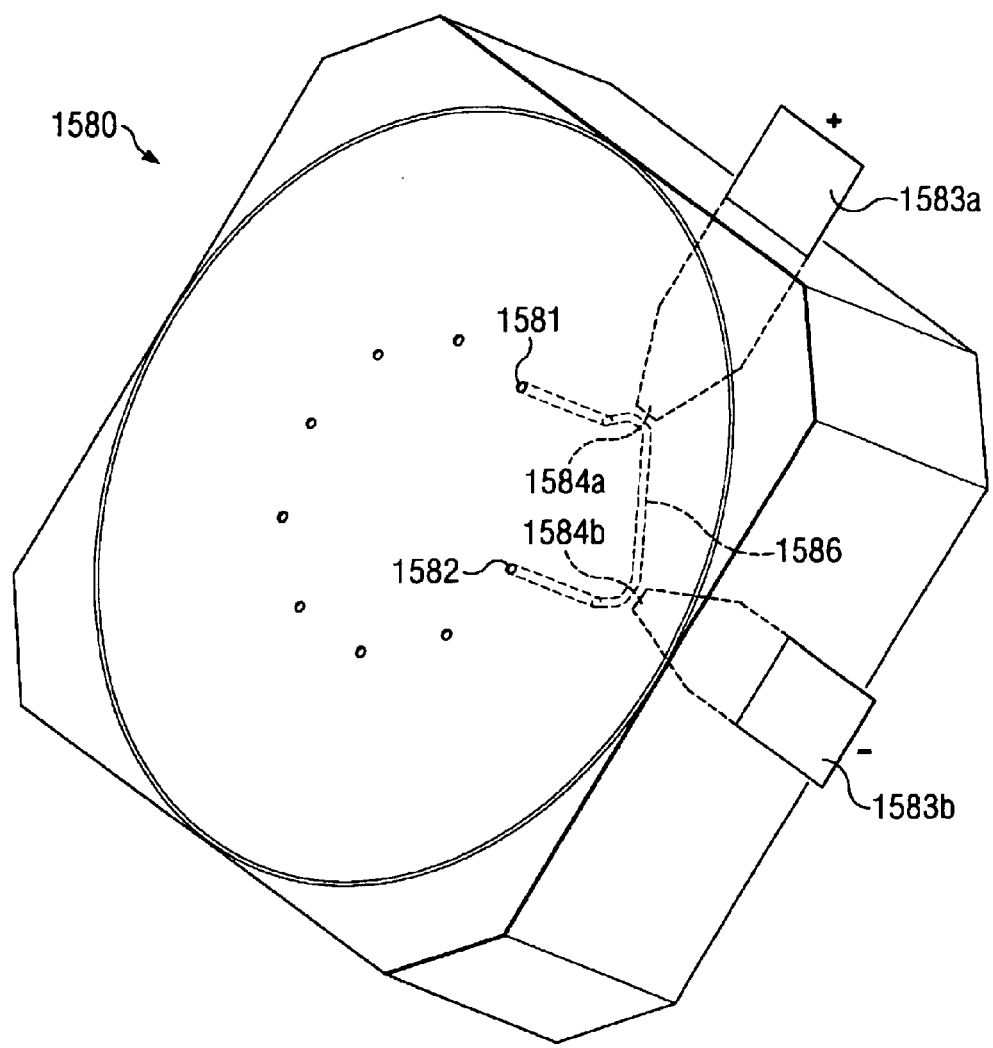
FIG. 15H shows one element of an embodiment of the invention.

Now referring to FIG. 15H, still another alternative element 1580 is shown. Element 1580 includes ports 1581 and 1582, which are in fluid communication with a detection loop 1586. Each of the ends of the detection loop 1585 are within close proximity of sensors 1584*a* and 1584*b*. As shown in FIG. 15H, the sensors 1584*a* and 1584*b* are in turn electrically connected to terminals 1583*a* and 1583*b*, respectively. By selectively applying an electric voltage across terminals 1583*a* and 1583*b*, the operator can effectively use the element 1580 as an electro-osmotic pump for the sample within the detection loop 1585. Such an effect provides the benefit of allowing selective control of the movement and flow of fluid moving through the system.

Figure 15I:
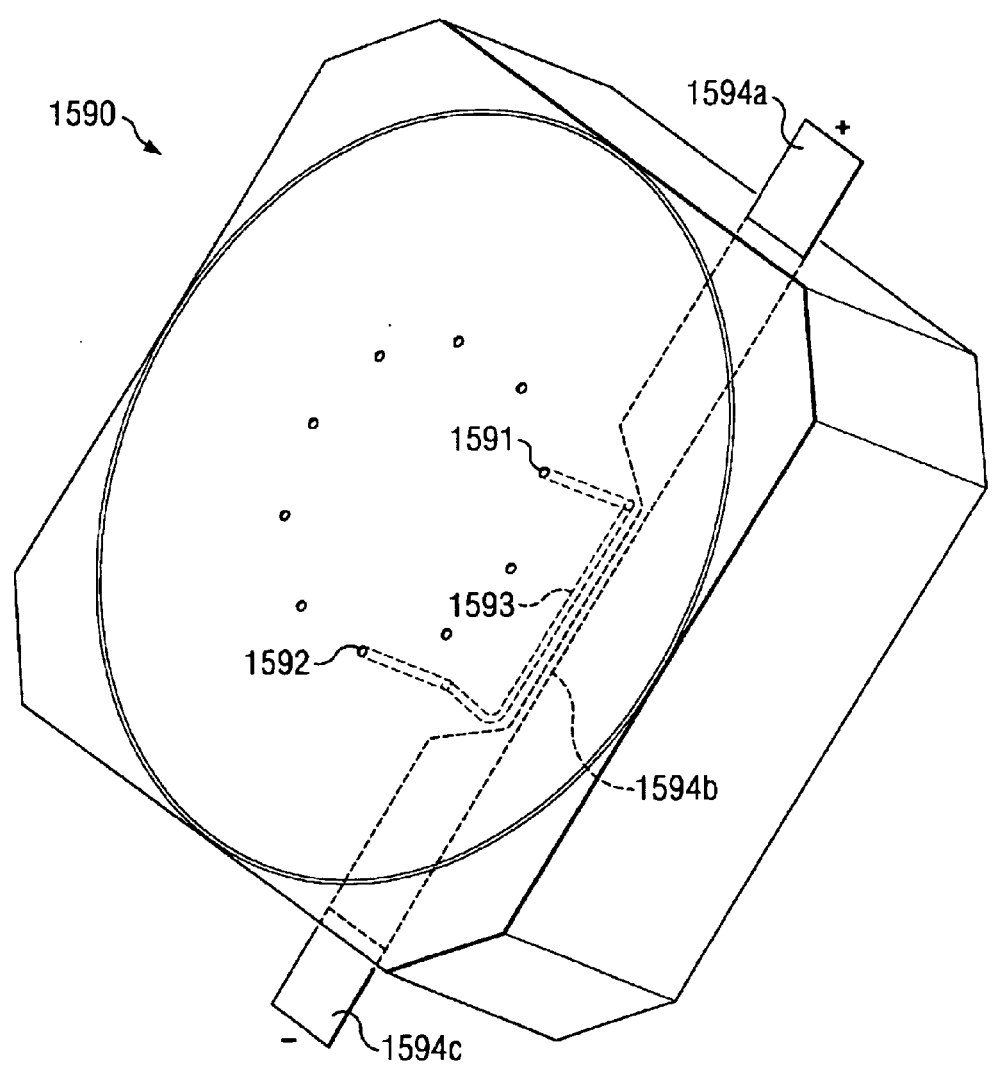
FIG. 15I shows one element of an embodiment of the invention.
Figure 16D:
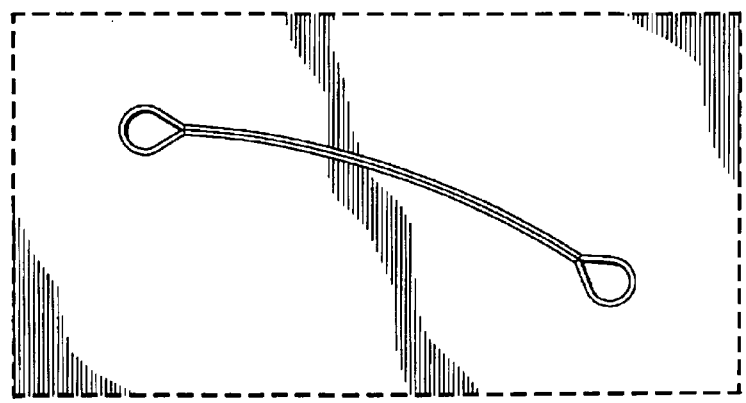
FIG. 16D is a detailed top view of a portion of the alternative rotor 26'.
Figure 16E:
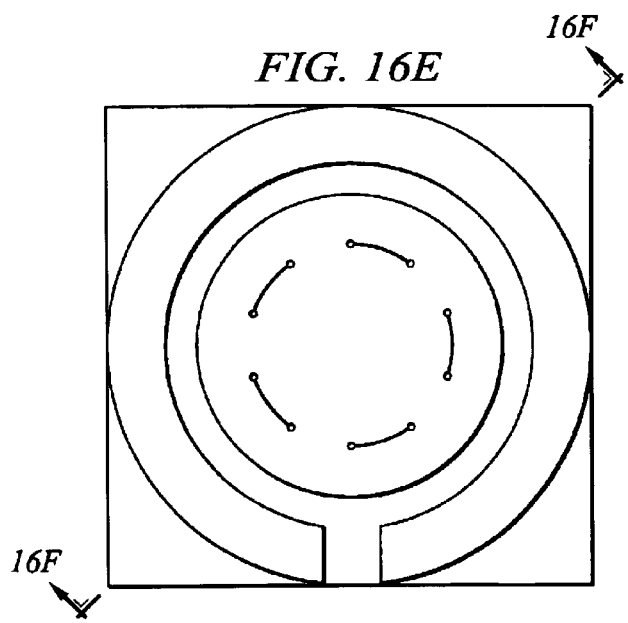
FIG. 16E is another top view of the alternative rotor 26'.
Figure 16F:
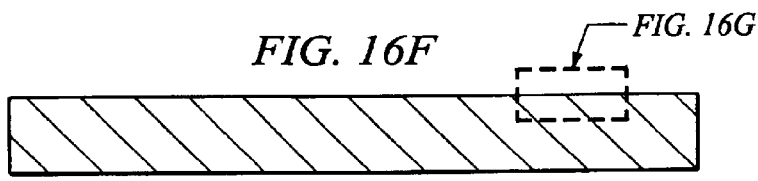
FIG. 16F is a sectional view of the alternative rotor 26' taken along line 16F—16F.

In FIG. 15I, an alternative element 1590 is shown. Element 1590 includes ports 1591 and 1592 which are in fluid communication with a temperature control loop 1593. Located and positioned in close proximity to the loop 1593 is an electrical temperature control element 1594*b*. The element 1594*b* can be used to selectively heat or chill the sample located in loop 1593 by selectively applying an electric voltage across terminals 1594*a* and 1594*b*, respectively, which are electrically connected to the element 1594*b*. Thus, element 1590 can be used to allow the operator to selectively control the temperature of the sample located in loop 1593, such as by heating or chilling the sample.

While the present invention has been shown and described in its preferred embodiment and in certain specific alternative embodiments, those skilled in the art will recognize from the foregoing discussion that various changes, modifications, and variations may be made thereto without departing from the spirit and scope of the invention as set forth in the claims. Hence, the embodiment and specific dimensions, materials and the like are merely illustrative and do not limit the scope of the invention or the claims herein.

We claim:

1. A valve for micro-fluidic analysis, comprising:
   a main valve body;
   a moveable rotor, having at least a portion located within said body, and having a face;
   a first element located within said body and having first and second sides, with the first side adjacent to one face of said rotor, and having at least one LC feature;
   a second element located within said body and having first and second sides, with the first side adjacent to the second face of said first element, and having at least one LC feature;
   a stator located within said body, having openings therethrough and having a face which is adjacent to one face of said second element;
   means for allowing selective rotation of said rotor; and
   means for selectively allowing for fluid communication between the openings of said stator and at least one of the LC features of said first and second elements.

2. The valve according to claim 1 wherein at least one of the LC features of said first and second elements comprises a plurality of sample loops.

3. The valve according to claim 2 wherein the sample loops comprise grooves on the face of said first element.

4. The valve according to claim 2 wherein the sample loops comprise grooves in the face of said second element.

5. The valve according to claim 2 wherein the sample loops are of different volumes.

6. The valve according to claim 1 wherein at least one of the LC features of said first and second elements comprises a column.

7. The valve according to claim 1 wherein at least one of the LC features of said first and second elements comprises a detector.

8. The valve according to claim 1 wherein said first element comprises at least one sample loop and at least one column.

9. The valve according to claim 1 wherein said second element comprises at least one sample loop and at least one column.

10. The valve according to claim 1 wherein at least one of the LC features of said first and second elements comprises a mixer.

11. A valve for micro-fluidic analysis, comprising:
    a main valve housing having a first end with a plurality of ports therethrough;
    a moveable rotor positioned at least partially within said housing having a first end.
    an element having first and second faces, with the first face adjacent to the first end of said rotor and adapted for movement responsive to movement of said rotor, wherein the second face of said element comprises at least two LC features which can be selectively positioned to be in fluid communication with at least one of the ports of said housing.

12. The valve according to claim 11 wherein at least one of the LC features of said element comprises a column.

13. The valve according to claim 12 wherein at least one of the LC features of said element comprises a sample loop.

14. The valve according to claim 13 wherein the sample loop comprises at least one groove in the second face of said element.

15. The valve according to claim 11 wherein at least one of the LC features of said element comprises a heating element.

16. The valve according to claim 11 wherein at least one of the LC features of element comprises an electro-osmotic pump.

17. The valve according to claim 11 further comprising:
    a plurality of tubes which allow fluid communication via the plurality of ports of said housing, wherein at least one end of one of said tubes in fluid communication with at least one of the LC features of the said element.

18. The valve according to claim 17 wherein a plurality of the ends of tubes are fluid communication with a least one of the LC feature of said element.

19. A method of micro-fluidic analysis, comprising the steps of:
    providing a valve which comprises within its housing a plurality of elements, each of the elements providing at least one LC feature, with the elements stacked together with the housing, wherein each of said elements is adapted to be selectively positioned within said valve; and
    selectively positioning at least one of the elements to engage at least one of the LC features provided by the first element.

20. The method according to claim 19 further comprising the step of selectively positioning a second of the plurality of elements to engage at least one of the LC features provided by the second element.

* * * * *